(12) United States Patent
McBride et al.

(10) Patent No.: US 6,268,546 B1
(45) Date of Patent: *Jul. 31, 2001

(54) OVARY-TISSUE TRANSCRIPTIONAL FACTORS

(75) Inventors: Kevin McBride; David Stalker, both of Davis, CA (US)

(73) Assignee: Calgene LLC, Davis, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/487,087

(22) Filed: Jun. 7, 1995

Related U.S. Application Data

(63) Continuation-in-part of application No. 07/998,158, filed on Dec. 29, 1992, now Pat. No. 5,530,185, which is a continuation-in-part of application No. 07/554,195, filed on Jul. 17, 1990, now Pat. No. 5,175,095, which is a continuation-in-part of application No. 07/382,518, filed on Jul. 19, 1989, now abandoned.

(51) Int. Cl.$^7$ .............................. A01H 1/00; C12N 5/00; C07H 21/04
(52) U.S. Cl. ..................... 800/282; 800/287; 800/278; 435/410; 536/23.5; 536/23.6; 536/24.1
(58) Field of Search .................... 800/205, DIG. 27; 536/23.2, 23.7, 24.1; 435/172.3, 320.1, 419; 935/64

(56) References Cited

U.S. PATENT DOCUMENTS

| | | | |
|---|---|---|---|
| 4,752,301 | * 6/1988 | Koch ........................ | 8/653 |
| 4,801,540 | 1/1989 | Hiatt ...................... | 435/172.3 |
| 4,943,674 | 7/1990 | Houck .................... | 800/205 |
| 5,005,863 | 4/1991 | Umbeck ................ | 800/205 |
| 5,159,135 | 10/1992 | Umbeck ................ | 800/205 |
| 5,360,726 | * 11/1994 | Raikhel ................. | 435/172.3 |
| 5,487,991 | * 1/1996 | Vandekerckhove et al. ..... | 435/172.3 |
| 5,495,070 | * 2/1996 | John .................... | 800/205 |
| 5,500,365 | * 3/1996 | Fischhoff et al. .......... | 435/240.4 |
| 5,530,185 | * 6/1996 | Martineau et al. ........ | 800/205 |
| 5,530,189 | * 6/1996 | Ausich et al. .......... | 800/205 |

FOREIGN PATENT DOCUMENTS

| | | |
|---|---|---|
| 0 198 288 A2 | 10/1986 | (EP) . |
| 0 255 378 A2 | 2/1988 | (EP) . |
| 0 363 792 A1 | 4/1990 | (EP) . |
| 0 409 629 A1 | 1/1991 | (EP) . |
| 0 631 128 A1 | 1/1995 | (EP) . |
| 88/09334 | 12/1988 | (WO) . |
| WO 89/08145 | 9/1989 | (WO) . |
| 89/12386 | 12/1989 | (WO) . |
| WO 91/13078 | 9/1991 | (WO) . |
| WO 91/13980 | 9/1991 | (WO) . |
| WO 92/14831 | 9/1992 | (WO) . |
| WO 92/15675 | 9/1992 | (WO) . |
| WO 93/02195 | 2/1993 | (WO) . |
| WO 96/26639 | 1/1995 | (WO) . |
| WO 95/06128 | 3/1995 | (WO) . |
| WO 95/13386 | 5/1995 | (WO) . |
| WO 95/16783 | 6/1995 | (WO) . |
| WO 96/13149 | 5/1996 | (WO) . |

OTHER PUBLICATIONS

U Homeyer et al. (1989) Plant Physiology 89: 1388–1393.*
PN Benfey et al (1990) Plant Cell 2: 849–856.*
T. Link (Oct. 22, 1989) Oregonian p. L03*
JNM Mol et al (1989) Plant Molecular Biology 13: 287–294.*
S Hart et al (1992) J Gen Microbiology (1992) 138: 211–216.*
MC Deeley et al (1981) J Bacteriology 147: 787–796.*
Misawa, N., et al. "Expression of an Erwinia phytoene desaturase gene not only confers multiple resistance to herbicides interfereing in carotenoid biosynthesis but also alters xanthophyll metabolism in transgenic plants" *The Plant Journal* vol. 6, No. 4:481–489 (1994).
Kavanagh, T.A., et al.: "Targeting a foreign protein to cholorplasts using fusions to the ransit peptide of a chlorophyll A/B protein" *Molecular and General Genetics* vol. 215, No. 1:38–45 Dec. 1988.
Pang, S–Z., et al: "Use of the signal peptide of *Pisum vicilin* to translocate beta–glucouronidase in *Nicotiana tabacum*" *Gene* vol. 112:229–234 (1992).
Fray, R.G. et al: "Identification and genetic analysis of normal and mutant phytoene synthase genes of tomato by sequencing, complementation and co–suppression", *Plant Molecular Biology* vol. 22:589–602 (1993).
John, M., et al.: "Genes for Jeans: Biotechnological Advances in Cotton" *Trends in Biotechnology* vol. 10, No. 5:165–170 (1992).
John, M.D., et al: "Re–engineering cotton fibre" *Chemistry and Industry* p. 676–679 (1994).
Abstract: Derwent Publics Ltd., London, G.B. XP002020286 & JP,A,02 104 773 (Nagase Sangyo KK), 17 (Apr. 1990).

(List continued on next page.)

Primary Examiner—Karen M. Hauda
Assistant Examiner—Joseph Woitach
(74) Attorney, Agent, or Firm—Barbara Rae-Venter; Jennifer Wahlsten; Rae-Venter Law GroupPC

(57) ABSTRACT

Novel DNA constructs are provided which may be used as molecular probes or inserted into a plant host to provide for modification of transcription of a DNA sequence of interest in ovary tissue, particularly in very early fruit development. The DNA constructs comprise a transcriptional initiation regulatory region associated with gene expression in ovary tissue from immediately prior to anthesis through flower senescence.

22 Claims, 11 Drawing Sheets

OTHER PUBLICATIONS

Kohel, R.J.,: "Genetic analysis of fiber color variants in Cotton" *Crop Science* vol. 25:793–797 (1985).

Graham, et al., Journal of Biological Chemistry (1985) vol. 260, No. 11:6561–6564.

John and Crow, Proc. Natl. Acad. Sci. (USA) (1992) vol. 89::5769–5773.

Kridl, et al., Seed Science Research (1991) vol. 1:209–219.

Radke, et al., Theor. Appl. Genet. (1988) vol. 75:685–694.

Radke, et al., Plant Cell Reports (1992) vol. 11:499–505.

Murai, et al., (1983) Science 222: 476–482.

Larkins, et al., (1985) J. Cell Biochem. Suppl. 9C:264.

Barker, et al., (1983) Plant Mol. Biol. 2:335–35.

McCormick, et al., 91987) Tomato Biotechnol., Nevins, et al., New York, pp. 255–265.

Piechulla, et al., (986) Plant Mol. Biol. 7:367–376.

Grierson, et al., (1986) Nucleic Acids Res. 14:8585–8603.

McCormick, et al., (2986) Plant Cell. Rep. 5:81–84.

Bird, C.R. et al., "The tomato polygalaturonase gene and ripening–specific expression in transgenic plants" Plant Molecular Biology 11:651–662 (1988).

Hiatt, W.R., et al., "Expression of selected genes during tomato fruit maturation and ripening" J.Cell Biochem Supp. O:148 (1988).

Benfey, P.N. and Chua, N., Regulated Genes in Transgenic Plants Science 244:174–181 (1989).

An, G. et al., "Organ–specific and developmental regulation of the nopaline synthase promoter in transgenic tobacco plants" Chemical Abstracts 110:122.

Martineau, B. and Houck, C.M., "Wound–Inducible Expression of a Gene From Tomato" J. of Cellular Biochemistry 14E:306 (1990).

Hass, G.M. and Hermodson, M.A., "Amino Acid Sequence of a Carboxypeptidase Inhibitor from Tomato Fruit" Biochemistry 20:2256–2260 (1981).

Gasser, C.S. et al., "Analysis of Floral Specific Genes," J.Cellular Biochem 12C:137 (1988).

Goldberg, R.B., "Plants: Novel Development Processes" Science 240:1460–1467 (1988).

Bernan, et al., Gene (1985) 37:101–110.

dellaCioppa et al., Bio/Technology (1990) 8–634–638.

Martineau et al., Mol. Gen. Genet. (1991) 228:281–286.

Chrispeels et al., Cell (1992) 68:613–616.

USSN 07/998,158 filed Dec. 29, 1992.

* cited by examiner

```
  1  AAAAAAACAAAAAACATTTCTAATCTTTTTCACTCATTCCATGGCTCGTCGTTCCATTTCTTCATGGCATTT   69
     TTTTTTGTTTTTGTAAAGATTAGAAAAAGTGAGTAAGGTACCGAGCAAGGTAAAAGAAGTACCGTAAA
     LysLysThrLysThrPheLeuIlePhePheThrHisSerMETAlaArgSerIlePhePheMETAlaPhe

70  TTGGTCTTGGCAATGATGCTCTTTGTTACCTATGAGGTAGAAGCTCAGCAAATTGCAAAGCACCAAGC   138
     AACCAGAACCGTTACTACGAGAGAAACAATGATACTCCATCTTCGAGTCGTCGTTAAACGTCGTTCG
     LeuValLeuAlaMETMETLeuPheVALThrTyrGluValGluAlaGlnIleCysLysAlaProSer

139  CAAACTTTCCCAGGATTATGTTTTATGGACTCATCATGTAGAAAAATATTGTATCAAAGAAATTTACT   207
     GTTTGAAAGGGTCCTAATACAAAATACCTGAGTAGTACATCTTTTATAACATAGTTTCTCTTAAATGA
     GlnThrPheProGlyLeuCysPheMETAspSerSerCysArgLysTyrCysIleLysGluLysPheThr

208  GGTGGACATTGTAGCAAACTCCAAAGAAGTGTCTATGCACTAAGCCATGTGTATTGACAAAATCTCA   276
     CCACCTGTAACATCGTTTGAGTTTCCTTCACAGATACGTGATTCGGTACACATAAACTGTTTTAGAGT
     GlyGlyHisCysSerLysLeuGlnArgLysCysLeuCysThrLysProCysValPheAspLysIleSer

277  AGTGAAGTTAAAGCAACTTTGGGTGAGGAAGCAACAAAAACTCTAAGTGAAGTTGTGCTTGAAGAGATT   345
     TCACTTCAATTTCGTTGAAACCCACTCCTTCGTTTGAGATTCACTTCAACACGAACTTCTCCTAA
     SerGluValLysAlaThrLeuGlyGluGluAlaLysThrLeuSerGluValValLeuGluGluIle

346  ATGATGGAGTAATAATTAAGTGAGGTTAAATAAGGATTTTGAGTGTCAAAAAAAACAAAATTAATAAAG   414
     TACTACCTCATTATTAATTCACTCCAATTTATTCCTAAAACTCACAGTTTTTTTTGTTTTAATTATTTC
     METMETGlu  ·  · LeuSerGluValLys ·  GlyPhe · ValSerLysThrLysLeuIleLys
```

Figure 1A

415  TGTTGCCTTTTCTTATTAGGGTAGCTTGTGATGTGTGTGTTAGTATTGGCCTATAGTAGCCATTTGACAC
     ACAACGGAAAAGAATAATCCCATCGAACACTACAACACAATCATAACCGGATATCATCGGTAAACTGTG       483
     CysCysLeuPheLeuLeuGly · LeuValMETLeuCys · TyrTrpProIleValAlaIle · His

484  ATTAAATAAGTTTGTGACACATCATTAATCCTTATGTATGTTTAATGAAAAATGATCGACTACG
     TAATTTATTCAAACACTGTGTAGTAATTAGGAATACATACATACAAAATTACTTTTTACTAGCTGATGC       552
     IleLys · ValCysAspThrSerLeuIleLeuMETTyrValCysPheAsnGluLys · SerThrThr

553  ATCTTTAATTTT       564
     TAGAAATTAAAA
     IlePheAsnPhe

Figure 1B

```
   1 GCTCCACTACTCTCATCACTTTAGTTCATCAAGCCTTCTTTTATACCAA   49
  50 GGCATCATCAATCTCATTAACAAAGTAGATTAGGGTTTTTCAAGATTTA   98
  99 GGATTCAATAGCTTCATCATGCTTATTTATCACAATTATATAATCACA  147
 148 TTCATACAAGCATACAATTAAGCATATAGAAGGGTTTACAATACTACCC  196
 197 AATACATATCATTCGCTATTAAGAGTTTACTACGAATAGCATAAACCAT  245
 246 AACCTACCTCCACCGAAGAATCGCGATCAAACAATCTACTTTCCCAAAG  294
 295 CTGCGTTCTTCTTCGTTTTCTCTCTCTTGATCGTTCGTTTCTCCCTC   343
 344 TCTTTGTTCTTTCTATTTTCTTATTCAAACCCTCTTTCTTTTACCCTA   392
 393 ATTAGTATATAATTAAGTATAAAAGATGATAAAATACCCCATCTATTTG  441
 442 TTTGAAGGTTATCTCTTTTAGCCCCCAAGTAATTGAATTATTAACATTA  490
 491 AACCACTAACTTTATAATTATAAGCAGGAATAGTCCAAAACGCCCCTTA  539
 540 AAATATTTAACAGAAATCCGACCCAGTCAGGGTCACGCAGCCTGTANCG  588
 589 GNNCACAACTGTGACGGTCCGTCCTGCATGGCCGTCACAAAGTTCAGAG  637
 638 AGTTAATTTCTGTGGAAGATGTGTANGGTNGTCGTGCCCACGACGGTCC  686
 687 GTCCTGTCATTTCGTTACGAAGTTCAGAGAGTCGATTTCAGTACCCAAA  735
         EcoRI
           |
 736 TTTCAGAATTCTAAGTGTTTTGGAACGAGACCCCNCGGTCCGTCGTGCC  784
              BamHI SalI
                |    |
 785 CATGACGGTTCGTCGTGGGATCCGTCGACTCAGCCAGTTTTTCCAAAAT  833
 834 TAAAATCTGCTGCTCAAAACGACTAAACAGGTCGTTACAAAGTACTCAA  882
 883 TCAAATAAAAGAATAAATTCTTTTCCAAATACATATATTGTTTATAGG   931
 932 ACAGTGTTAACAGGGAAATGTAATCGTTGCCTCAATCGATTTTTTTTT   980
            BglII
              |
 981 TGAAATTAAGATTGATTAGATCTTCTTTAAGATAACAATGTCTCAAAGA 1029
1030 TAAATTGAATGAATGAATTAGCTATATTATCATTTGAAAAGAAATTACT 1078
1079 AAAACAGATTGATAATAAAATAATAATAAATGACTTTGCATCTAAAATA 1127
1128 GCTAGAAAGCAGATTTTTAAATAAAAATACATATGATAAAAAAAGATA  1176
1177 AATTAGAGTCATCCCATAAATTTCGCTTTAGGCCCCCAATGTTGTTAAG 1225
1226 TCGGCCCTGAAAATAGGAATGGTATTAAATATTTTGTTTTGATTTCACA 1274
1275 CTTGATATTTGACATTCATATTAGAAAATAATTAAATTTATATTCGTGT 1323
1324 AGAGTGGTCTCACATTAATGGGTAAAATATTTCCACACAAAACTATTT  1372
1373 TACAATCATAGCTAGAATCTGAAATATCTAATGTACTCCACCCAATTAA 1421
1422 TTAAAGATGATTTTTTGCTTAAATAATAAAAATATGTCTATTGCCAAA  1470
1471 CTACTAATAGATGTACTCACAAAAAAATAAAATAAAAAATCAAGTGTA  1519
1520 TATACAATGATTCGGAAGGCCATTTTGAAAATTTTCATAAAATGACCG  1568
1569 TTTTACCCGTTCACAATTGTTGTTTCAGCATTTTGTTTGGTTTGTGGA  1617
                                          HindIII
                                             |
1618 TTTGGTTATGGAAGTTCAATAAAAAGTTGTGGTTTTATAAGCTTTGGAG 1666
1667 TTTTGAAAGGTTTAAGTTGATTAAAAGTAGTTTTTAGTGTCAATTGGAG 1715
```

Figure 2A

```
1716 TTTCGTGTCTTGAAATAAATTTTATCACTTGCATTAGTTTCAAAATGTC 1764
1765 GAGTTTGGTTAAGTAGAGGTTTTTTTCATTCGGAGTTTTTTTATGAATT 1813
1814 TAAAATGTTAAGCTGAAAGTTTATGAAATTTTAGCCTTTGAGTTAATTT 1862
1863 TGATGCTTGAATTAAATTTTTGAGAATTTTTTTGAAATCTGGGGATAAT 1911
1912 GTTAGGTCTTAGAGAAGTCTGGTTGAATTTTCATAGCTCAAGAGATTAG 1960
1961 TTTTGACTTTTTAGGCATTTTGTTGGTTTATTACGATTTTCACGGACTT 2009
2010 TCGAATTAAGGAGACTTCAAAATTCATATTTAATGGTTCGTGTGTTCGT 2058
2059 TAGTTTTAAAAATCGTGTCTTTATAAGGATTTATACTTAAAAAAATAAA 2107
2108 ATAAAATAAAGTACTACTAACATGTAATTCTGTCATAAGATAAGGTTGT 2156
2157 ACATTTAGGACTATTTGAATATTCATCAAAATAAAAAAAGTAGAGAT 2205
2206 GATAGTAATATAAATATTTATTTTTGATTTTACATTTGATATTTTAATA 2254
2255 CTAACAATATGACATAATAAAATTTGTATTCAGATTGTAAATATTCCC 2303
2304 TAAAAAAGATACTTTTACTGTGGTGGCTCAAATTCAAAATTTTCTAAG 2352
2353 AAAAACTACTAATAATTGATTTCTAATTAAAATTTCGATATATATAT 2401
2402 ATATATATATATATCATAATATACTTCACCTACCTCAATTATTATTA 2450
2451 TTTTCTTTTTTTTTACTTCACATATTTTGGSCSACCAATTTTTTTTT 2499
2500 TAACTTTTTGGTCTTACTCTTATTTCACTCCCTATAAATAACTCCCAT 2548
2549 TGTGTGATATTTTTATTCACAACTCTAACTTACAATCTTTCTTATTATT 2597
                     NcoI
                       |
2598 AAAAAAAACAAAAACATTTCTAATCTTTTTCACTCATTCCATGGCTCGT 2646
2647 TCCATTTTCTTCATGGCATTTTTGGTCTTGGCAATGATGCTCTTTGTTA 2695
2696 CCTATGgtttgtcttcataatttattcctctaaaatcatcgcaataaaa 2744
2745 aaaaatgtaacgaagcagacatcagtaaaccgtttaaataaaccctaa 2793
2794 aaaaattgtgaattgatattacttgctatacgtttaacaactatgataa 2842
2843 aaaaaccctaaaatatacttatttcgatttcgtctctctcatgttattc 2891
2892 taactattttttgtgtgtgaatgattgtagAGGTAGAAGCTCAGCAAAT 2940
2941 TTGCAAAGCACCAAGCCAAACTTTCCAGGATTATGTTTTATGGACTCA 2989
2990 TCATGTAGAAAATATTGTATCAAAGAGAAATTTACTGGTGGACATTGTA 3038
3039 GCAAACTCCAAAGGAACTGTCTATGCACTAAGCCATGTGTATTTGACAA 3087
3088 AATCTCAAGTGAAGTTAAAGCAACTTTGGGTGAGGAAGCAAAAACTCTA 3136
3137 AGTGAAGTTGTGCTTGAAGAAGAGATTATGATGGAGTAATAATTAAGTG 3185
3186 AGGTTAAATAAGGATTTTGAGTGTCAAAAAAACAAAATTAATAAAGTG 3234
3235 TTGCCTTTTCTTATTAGGGTAGCTTGTGATGTTGTGTTAGTATTGGCCT 3283
3284 ATAGTAGCCATTTGACACATTAAATAAGTTTGTGACACATCATTAATCC 3332
3333 TTATGTATGTATGTTTTAATGAAAAATGATCGACTACGATCTTTAATTT 3381
3382 TATGTTTTACATTTAATTAATCACTTTCTGTTACGATTCATTTATCTAG 3430
3431 TTATGAATGAAATATAGAGTGATTTGAAGTAAGGAGCTAGTCTTCAAAC 3479
3480 AAAGACGTACATATGTACAAGTAGGGTACTATTAAACTTCTTTTTTAT 3528
```

Figure 2B pZ70

```
  1  ATTATTATTACCATGGCACAAAAATTTACTATCCTTTTCACCATTCTCCTTGTGGTTATTGCTGCTCAA   69
          METAlaGlnLysPheThrIleLeuPheThrIleLeuLeuValValIleAlaAlaGln
                                   Mature Protein Start 70  GATGTGATGGCACAAGATGCAACTCTGACGAAACTTTTTCAGCAATATGATCCAGTTTGTCACAAACCT  138
     AspValMETAlaGlnAspAlaThrLeuThrLysLeuPheGlnGlnTyrAspProValCysHisLysPro 139  TGCTCAACACAAGACGATTGTTCTGGTACGTTCTGTCAGGCCTGTTGGAGGTTCGCGGGACATGT      207
     CysSerThrGlnAspAspCysSerGlyGlyThrPheCysGlnAlaCysTrpArgPheAlaGlyThrCys
     Mature Protein End 208  GGGCCCTATGTTGGGCGGGGCGCCATGGCCGTGTGATTACAATTTCGTTGTTCTTCTTTTTCGACT      276
     GlyProTyrValGlyArgAlaMETAlaIleGlyVal 277  TTTTAATCCCAAGTGAATAAAGTCTAATTCGAAAAAAAGAAGAAAAAAGTATCTATGTCTGAGTTATATGT  345

346  TTTGTGGCTAATAAGAAATCGACTATGCTTGTTGATTTGATAAAAATTATGTCATTAGGGTGTGATATG   414

415  TAATCATCAAATTAAATAAAAATCATCGCATTGTGTGTG  453
```

Figure 4

OVARY-TISSUE TRANSCRIPTIONAL FACTORS

CROSS-REFERENCE TO RELATED APPLICATIONS

This application is a continuation in part of U.S. application Ser. No. 07/998,158 filed Dec. 29, 1992 now U.S. Pat. No. 5,530,185, which is a continuation in part of U.S. application Ser. No. 07/554,195 filed Jul. 17, 1990, now U.S. Pat. No. 5,175,095, which is a continuation-in-part of U.S. application Ser. No. 07/382,518, filed Jul. 19, 1989, now abandoned which applications are incorporated herein by reference.

INTRODUCTION

1. Technical Field

This invention relates to methods of using in vitro constructed DNA transcription or expression cassettes capable of directing ovary-tissue transcription of a DNA sequence of interest in plants to produce ovary-derived cells having an altered phenotype, and to methods of providing for or modifying existing color in various plant tissues or parts. The invention is exemplified by methods of using ovary tissue promoters for altering the color phenotype of cotton fibers, and cotton fibers produced by the method.

2. Background

In general, genetic engineering techniques have been directed to modifying the phenotype of individual prokaryotic and eukaryotic cells, especially in culture. Plant cells have proven more intransigent than other eukaryotic cells, due not only to a lack of suitable vector systems but also as a result of the different goals involved. For many applications, it is desirable to be able to control gene expression at a particular stage in the growth of a plant or in a particular plant part. For this purpose, regulatory sequences are required which afford the desired initiation of transcription in the appropriate cell types and/or at the appropriate time in the plant's development without having serious detrimental effects on plant development and productivity. It is therefore of interest to be able to isolate sequences which can be used to provide the desired regulation of transcription in a plant cell during the growing cycle of the host plant.

One aspect of this interest is the ability to change the phenotype of particular cell types, such as differentiated epidermal cells that originate in ovary tissue, i.e. cotton fiber cells, so as to provide for altered or improved aspects of the mature cell type. In order to effect the desired phenotypic changes, transcription initiation regions capable of initiating transcription only in early ovary development are used. These transcription initiation regions are active prior to the onset of pollination and are less active or inactive, before fruit enlargement, tissue maturation, or the like occur.

Relevant Literature

A class of fruit-specific promoters expressed at or during anthesis through fruit development, at least until the beginning of ripening, is discussed in European Application 88.906296.4, the disclosure of which is hereby incorporated by reference. cDNA clones that are preferentially expressed in cotton fiber have been isolated. One of the clones isolated corresponds to mRNA and protein that are highest during the late primary cell wall and early secondary cell wall synthesis stages. John Crow *PNAS* (1992) 89:5769–5773. cDNA clones from tomato displaying differential expression during fruit development have been isolated and characterized (Mansson et al., *Mol. Gen. Genet.* (1985) 200:356–361: Slater et al., *Plant Mol. Biol.* (1985) 5:137–147). These studies have focused primarily on mRNAs which accumulate during fruit ripening. One of the proteins encoded-by the ripening-specific cDNAs has been identified as polygalacturonase (Slater et al., *Plant Mol. Biol.* (1985) 5:137–147). A cDNA clone which encodes tomato polygalacturonase has been sequenced (Grierson et al., *Nucleic Acids Research* (1986) 14:8395–8603). Improvements in aspects of tomato fruit storage and handling through transcriptional manipulation of expression of the polygalacturonase gene have been reported (Sheehy et al., *Proc. Natl. Acad. Sci. USA* (1988) 85:8805–8809; Smith et al., *Nature* (1988) 334:724–726).

Mature plastid mRNA for psbA (one of the components of photosystem II) reaches its highest level late in fruit development, whereas after the onset of ripening, plastid mRNAs for other components of photosystem I and II decline to nondetectable levels in chromoplasts (Piechulla et al., *Plant Molec. Biol.* (1986) 7:367–376). Recently, cDNA clones representing genes apparently involved in tomato pollen (McCormick et al., *Tomato Biotechnology* (1987) Alan R. Liss, Inc., NY) and pistil (Gasser et al., *Plant Cell* (1989), 1:15–24) interactions have also been isolated and characterized.

Other studies have focused on genes inducibly regulated, e.g. genes encoding serine proteinase inhibitors, which are expressed in response to wounding in tomato (Graham et al., *J. Biol. Chem.* (1985) 260:6555–6560: Graham et al.,*J. Biol. Chem.* (1985) 260:6561–6554) and on mRNAs correlated with ethylene synthesis in ripening fruit and leaves after wounding (Smith et al., *Planta* (1986) 168:94–100). Accumulation of a metallocarboxypeptidase inhibitor protein has been reported in leaves of wounded potato plants (Graham et al., *Biochem & BioPhys. Res Comm.* (1981) 101:1164–1170).

Genes which are expressed preferentially in plant seed tissues, such as in embryos or seed coats, have also been reported. See, for example, European Patent Application 87306739.1 (published as 0 255 378 on Feb. 3, 1988) and Kridl et al. (Seed Science Research (1991) 1:209–219).

Agrobacterium-mediated cotton transformation is described in Umbeck, U.S. Pat. Nos. 5,004,863 and 5,159,135 and cotton transformation by particle bombardment is reported in WO 92/15675, published Sept. 17, 1992. Transformation of Brassica has been described by Radke et al. (Theor. Appl. Genet. (1988) 75;685–694; Plant Cell Reports (1992) 11:499–505.

Transformation of cultivated tomato is described by McCormick et al., *Plant Cell Reports* (1986) 5:81–89 and Fillatti et al., *Bio/Technology* (1987) 5:726–730.

SUMMARY OF THE INVENTION

Novel DNA constructs and methods for their use are described which are capable of directing transcription of a gene of interest in ovary tissue, particularly early in fruit development. The novel constructs include a vector comprising a transcriptional and translational initiation region obtainable from a gene expressed in ovary tissue and methods of using constructs including the vector for altering fruit phenotype. The fruit may be edible or non-edible. The method includes transfecting a host plant cell of interest with a transcription or expression cassette comprising a promoter which is active in ovary cells prior to, and during, the pollination stage of the fruit, then generating a plant, which is grown to produce fruit having the desired phenotype.

Constructs and methods of the subject invention thus find use in modulation of endogenous fruit products, as well as production of exogenous products and in modifying the phenotype of fruit and fruit products. The constructs also find use as molecular probes. In particular, constructs and methods for use in gene expression in cotton embryo tissues are considered herein. By these methods, novel cotton plants and cotton plant parts, such as modified cotton fibers, may be obtained.

Also provided in the instant application are constructs and methods of use relating to modification of color phenotype in plant tissues. Such constructs contain sequences for expression of genes involved in the production of colored compounds, such as melanin or indigo, and also contain sequences which provide for targeting of the gene products to particular locations in the plant cell, such as plastid organelles, or vacuoles. Plastid targeting is of particular interest for expression of genes involved in aromatic amino acid biosynthesis pathways, while vacuolar targeting is of particular interest where the precursors required in synthesis of the pigment are present in vacuoles. Production of melanin, for example, may be enhanced by vacuolar targeting in plant tissues which accumulate tyrosine in vacuoles. Transcriptional initiation regions for expression of color-related genes will be selected on the basis of the tissue for which color modification is desired.

DESCRIPTION OF THE DRAWINGS

FIG. 1 shows the DNA sequence of cDNA clone (SEQ ID NO. 1) pZ130. The sequences corresponding to the pZ7 cDNA clone are underlined.

FIG. 2 shows the sequence of the region of the Calgene Lambda 140 genomic clone (SEQ ID NO. 1) that overlaps with the pZ130 cDNA clone (this region is underlined) and a partial sequence of regions 5' and 3' to that region. The start of the pZ130 gene transcript is indicated by the underlined, boldfaced "A" at position 2567. An intron in the gene sequence is indicated by the lower case sequence from position 2702 through position 2921. Sites for common restriction enzymes are indicated.

The symbols in the sequence have the following meaning:

A=adenosine; C=cytosine; G=guanine; T=thymidine or uracil; R=A or G; Y=C or T or U; M=C or A; K=T or U or G; W=T or U or A; S=C or G; N=either C, T, A G or U; B=not A; D=not C; H=not G; V=not T or U.

Figure 3:
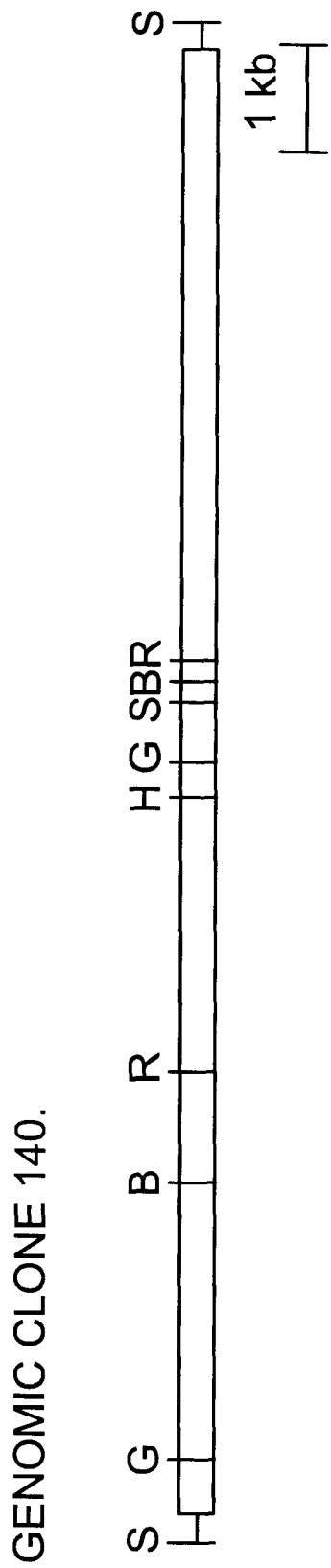

FIG. 3 shows a restriction map of Calgene Lambda 140. B:BamHI; G:BglII; H:HindIII; R:EcoRI; S:SalI.

FIG. 4 shows a complete DNA sequence of cDNA clone (SEQ ID NO. 3) pZ70. The sequences corresponding to the pZ8 cDNA clone are underlined. The start and end of the mature protein encoded by the pZ70 gene are also indicated.

Figure 5:
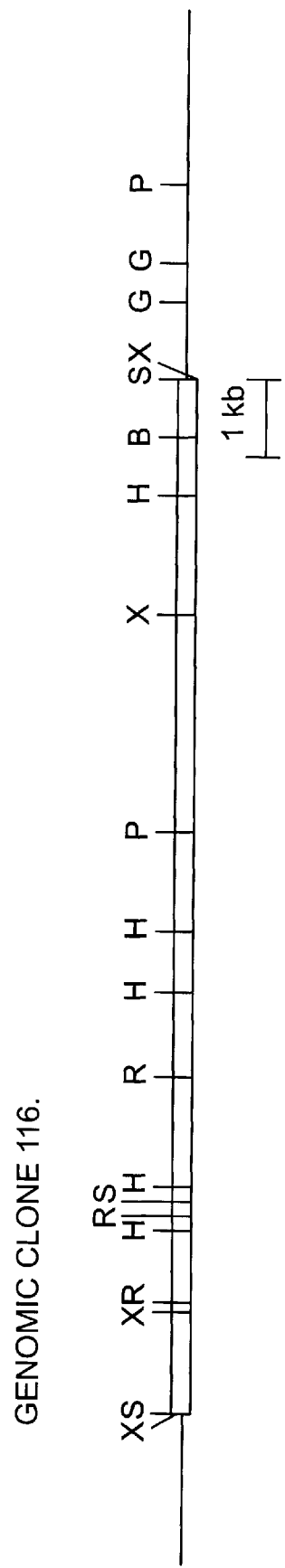

FIG. 5 shows a restriction map of Calgene Lambda 116. B:BamHI; G:BglII, H:HindIII; P:SphI; R:EcoRI; S:SalI; X:XbaI.

Figure 6A:
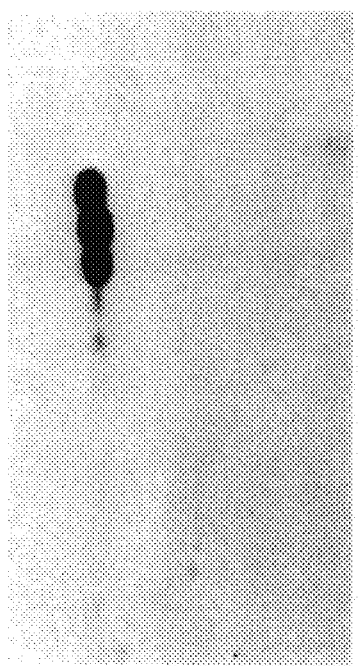
Figure 6B:
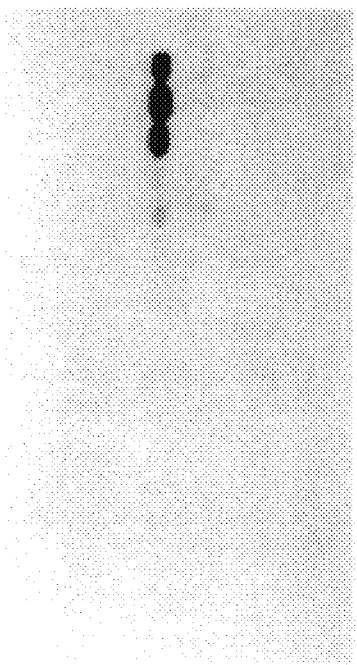
Figure 6C:
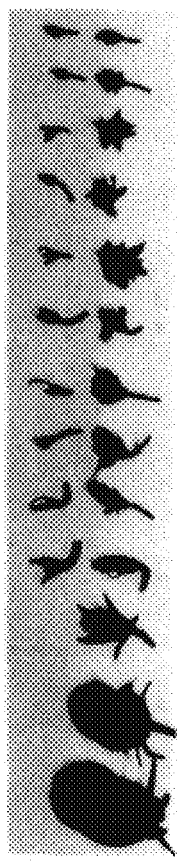

FIGS. 6A and 6B show the results of a Northern blot experiment illustrating a developmental time course of pZ7 (FIG. 6B) and pZ8 (FIG. 6A) RNA accumulation. The stages of UC82B fruit development (flowers and ovaries/fruit) are depicted in FIG. 6C Numbers 1 through 21 represent days post flower opening.

Figure 7A:
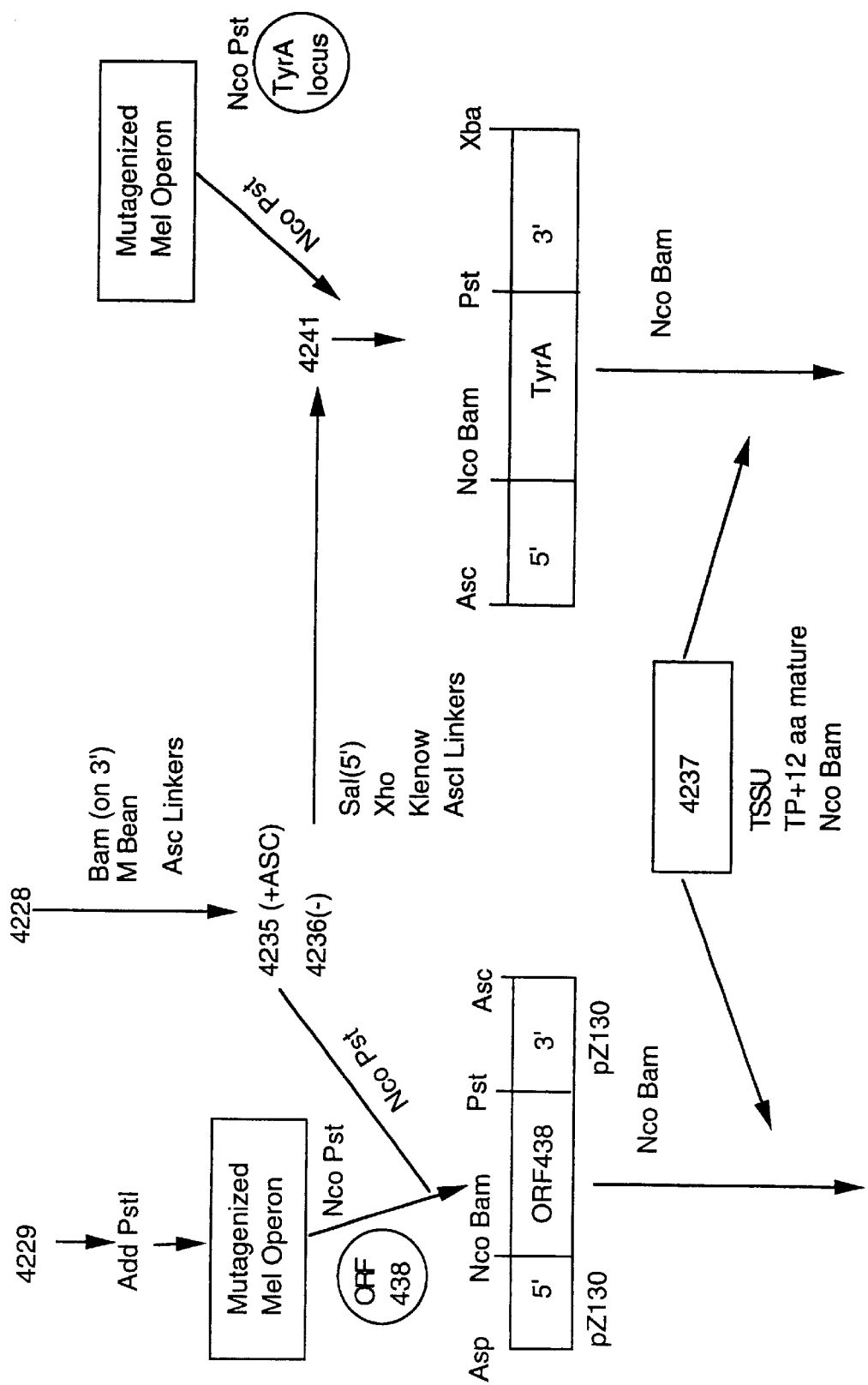
Figure 7B:
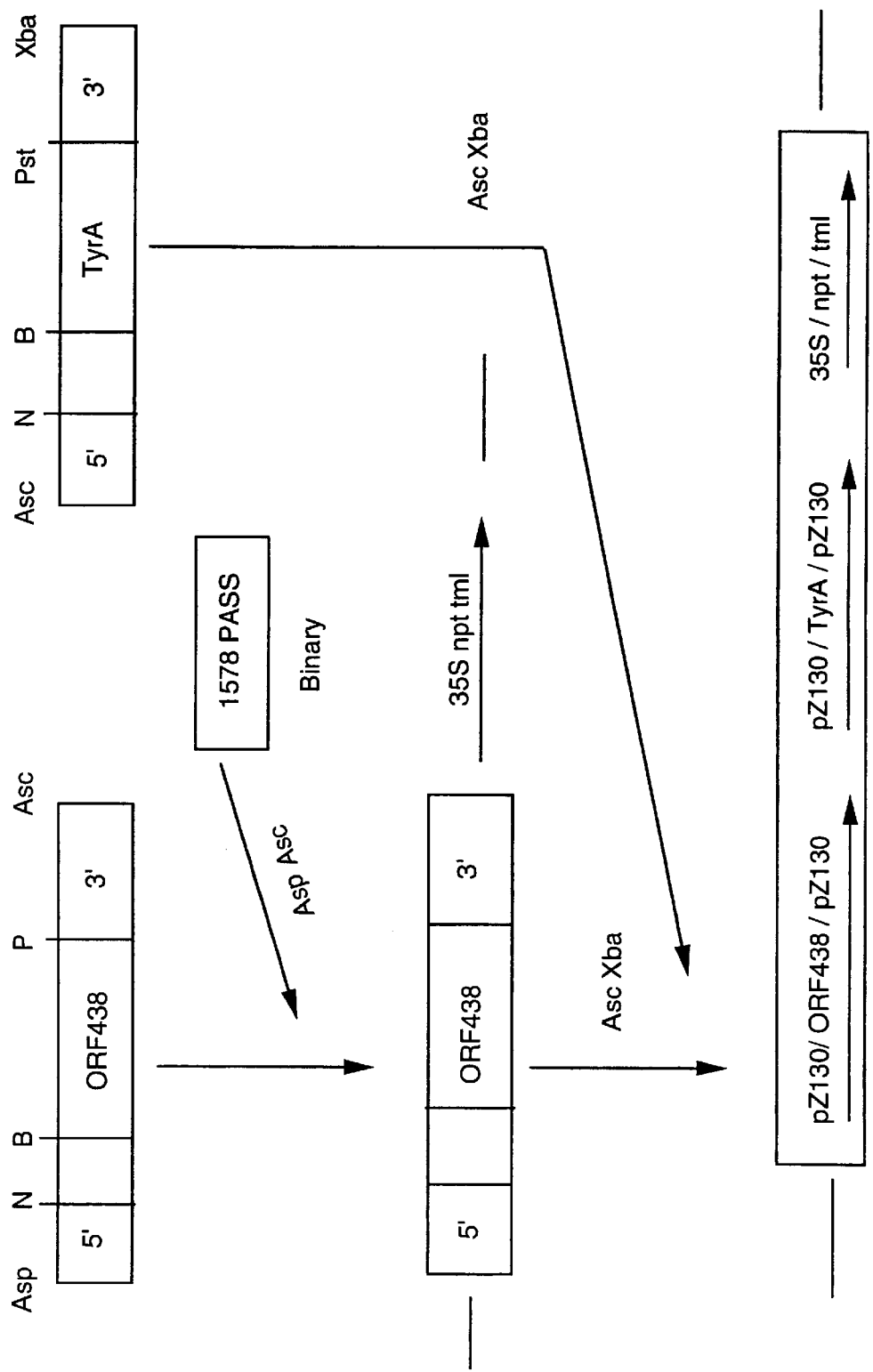

FIG. 7 shows a binary vector for plant transformation to express genes for melanin synthesis.

Figure 8:
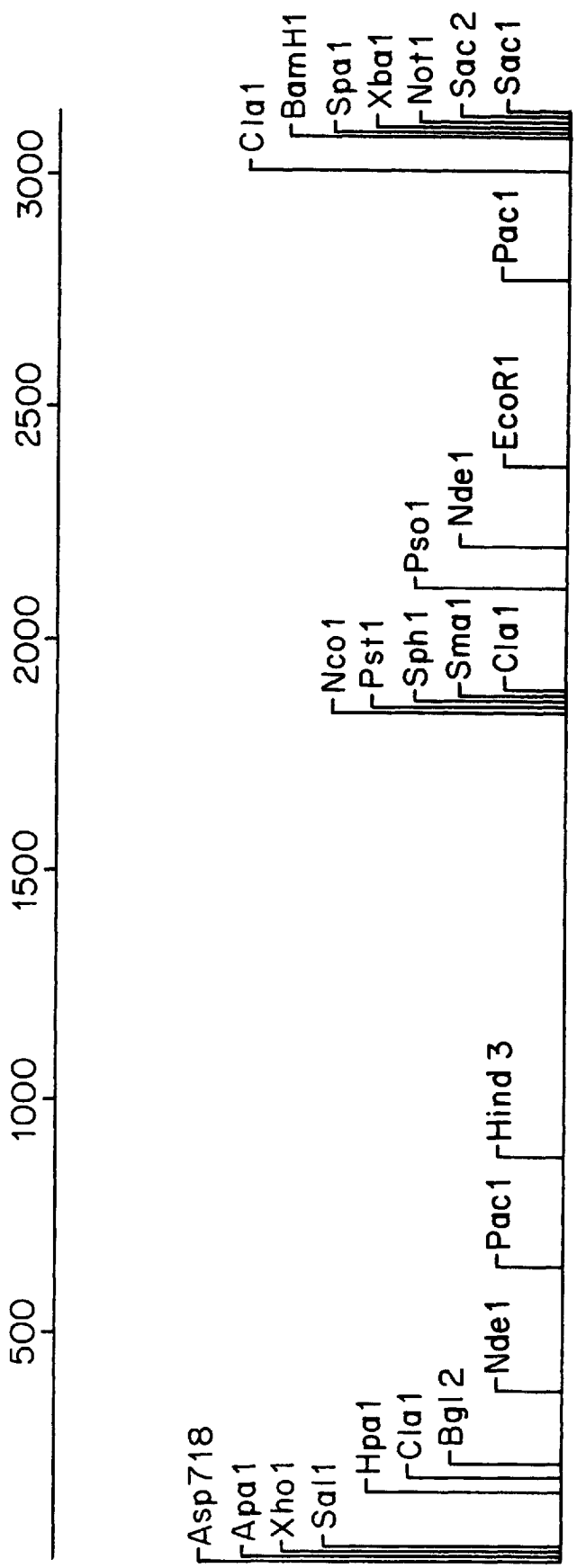

FIG. 8 shows a linker region site map.

DETAILED DESCRIPTION OF THE INVENTION

In accordance with the subject invention, novel constructs and methods for their use are described which may be used as molecular probes or inserted into a plant host to provide for transcription of a nucleotide sequence of interest in ovary cells as compared with other plant cells, generally preferentially in ovary cells to produce cells and plant parts having an altered phenotype. Of particular interest is the period of at least one to three days prior to anthesis through flower senescence.

The constructs include several forms, depending upon the intended use of the construct. Thus, the constructs include vectors, transcriptional cassettes, expression cassettes and plasmids. The transcriptional and translational initiation region (also sometimes referred to as a "promoter,"), preferably comprises a transcriptional initiation regulatory region and a translational initiation regulatory region of untranslated 5' sequences, "ribosome binding sites, "responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

The vectors typically comprise a nucleotide sequence of one or more nucleotides and a transcriptional initiation regulatory region associated with gene expression in ovary tissue. A transcriptional cassette for transcription of a nucleotide sequence of interest in ovary tissue will include in the direction of transcription, an ovary tissue transcriptional initiation region and optionally a translational initiation region, a DNA sequence of interest, and a transcriptional and optionally translational termination region functional in a plant cell. When the cassette provides for the transcription and translation of a DNA sequence of interest it is considered an expression cassette. One or more introns may be also be present.

Other sequences may also be present, including those encoding transit peptides and secretory leader sequences as desired. The regulatory regions are capable of directing transcription in ovary cells from anthesis through flowering but direct little or no expression after the initial changes which occur at the time surrounding pollination and/or fertilization; transcription from these regulatory regions is not detectable at about three weeks after anthesis. Further, ovary-tissue transcription initiation regions of this invention are typically not readily detectable in other plant tissues. Transcription initiation regions from ovary tissue that are not ovary specific may find special application. Especially preferred are transcription initiation regions which are not found at stages of fruit development other than pre-anthesis through flowering. Transcription initiation regions capable of initiating transcription in other plant tissues and/or at other stages of ovary development, in addition to the foregoing, are acceptable insofar as such regions provide a significant expression level in ovary tissue at the defined periods of interest and do not negatively interfere with the plant as a whole, and, in particular, do not interfere with the development of fruit and/or fruit-related parts. Also of interest are ovary tissue promoters and/or promoter elements which are capable of directing transcription in specific ovary tissues such as outer pericarp tissue, inner core tissues, integuments, and the like.

Transcriptional initiation regions which are expressible in ovary tissue at or near maximal levels during the period of interest of this invention, generally the flowering period of plant reproductive cycles, are preferred. Of particular interest is the period of at least one to three days prior to anthesis through flower senescence. The transcription level should be sufficient to provide an amount of RNA capable of resulting in a modified fruit. The term "fruit" as used herein refers to the mature organ formed as the result of the development of the ovary wall of a flower and any other closely associated parts. See Weirer, T. E., 1, ed., *Botany A Introduction to Plant Biology* (6th ed.) (John Wiley & Sons, 1982); Tootill & Backmore, *The Facts on File Dictionary of Botany* (Market Home Books Ltd., 1984). By "modified fruit" is meant fruit having a detectably different phenotype from a nontransformed plant of the same species, for example, one not having the transcriptional cassette in question in its genome.

Of particular interest are transcriptional initiation regions associated with genes expressed in ovary tissue and which are capable of directing transcription at least 24 hours prior to anthesis through flower senescence. The term "anthesis" refers herein to the period associated with flower opening and flowering. The term "flower senescence" refers herein to the period associated with flower death, including the loss of the (flower) petals, etc. Abercrombie, M., et al., *A Dictionary of Biology* (6th ed) (Penguin Books, 1973). Unopened flowers, or buds, are considered "pre-anthesis." Anthesis begins with the opening of the flower petals, which represents asexually receptive portion of the reproductive cycle of the plant. Typically, flowering lasts approximately one week in the tested UCB82 tomato variety. In a plant like cotton, flowering lasts approximately two weeks and the fiber develops from the seed coat tissue. It is preferred that the transcriptional initiation regions of this invention do not initiate transcription for a significant time or to a significant degree prior to plant flower budding. Ideally, the level of transcription will be high for at least approximately one to three days and encompass the onset of anthesis ("pre-anthesis").

It further is desired that the transcriptional initiation regions of this invention show a decreased level of transcriptional activity within 1–3 days after the onset of anthesis which does not increase, and preferably decreases over time. Fertilization of a tomato embryo sac, to produce the zygote that forms the embryo plant, typically occurs 2–3 days after flower opening. This coincides with a decrease in the activity of a transcriptional initiation region of this invention. Thus, it is desired that the transcriptional activity of the promoter of this invention significantly decrease within about two days after the onset of anthesis. Transcriptional initiation regions of this invention will be capable of directing expression in ovary tissue at significant expression levels during the preferred periods described above.

In some embodiments, it will be desired to selectively regulate transcription in a particular ovary tissue or tissues. When used in conjunction with a 5' untranslated sequence capable of initiating translation, expression in defined ovary tissue, including ovary integuments (also known as "ovule epidermal cells"), core or pericarp tissue, and the like, the transcriptional initiation region can direct a desired message encoded by a DNA sequence of interest in a particular tissue to more efficiently effect a desired phenotypic modification. For example, expression in ovary pericarp tissue, also known as the ovary wall and/or ovary core tissue, could result in useful modifications to the edible portions of many fruits, including true berries such as tomato, grape, blueberry, cranberry, currant, and eggplant; stone fruits (drupes), such as cherry, plum, apricot, peach, nectarine and avocado; and compound fruits (druplets), such as raspberry and blackberry. In hesperidium (oranges, citrus), such expression cassettes are expected to be expressed in the "juicy" portion of the fruit. In pepos, (such as watermelon, cantaloupe, honeydew, cucumber, and squash) the equivalent tissue is most likely the inner edible portions. In other fruits, such as legumes, the equivalent tissue is the seed pod.

The modification of analogous structures of non-edible fruit may also be of interest. Thus, of special interest are transcription initiation regions expressible in at least ovary outer pericarp tissue. For example, in cotton the analogous ovary structure is the burr of the cotton boll, in rapeseed it is the seed pod. In a like manner, regulating expression in ovary integuments and/or core tissue may result in useful modifications to the analogous fruit and related structures evolving there from, for example seed coat hairs, such as cotton fibers. Cotton fiber is a differentiated single epidermal cell of the outer integument of the ovule. It has four distinct growth phases; initiation, elongation (primary cell wall synthesis), secondary cell wall synthesis, and maturation. Initiation of fiber development appears to be triggered by hormones. The primary cell wall is laid down during the elongation phase, lasting up to 25 days postanthesis (DPA). Synthesis of the secondary wall commences prior to the cessation of the elongation phase and continues to approximately 40 DPA, forming a wall of almost pure cellulose. In addition to ovary tissue promoters, transcriptional initiation regions from genes expressed preferentially in seed tissues, and in particular seed coat tissues, are also of interest for applications where modification of cotton fiber cells is considered.

An example of a gene which is expressed at high levels in Brassica seed coat cells is the EA9 gene described in EPA O255 378. The nucleic acid sequence of a portion of the EA9 cDNA is provided therein, and can be used to obtain corresponding sequences, including the promoter region. An additional seed gene which is expressed in seed embryo and seed coat cells is the Bce4 Brassica gene. The promoter region from this gene also finds use in the subject invention; this gene and the corresponding promoter region are described in WO 91/13980, which was published Sept. 19, 1991. Fiber specific proteins are developmentally regulated. Thus, transcriptional initiation regions from proteins expressed in fiber cells are also of interest. An example of a developmentally regulated fiber cell protein, is E6 (John and Crow Proc. Nat. Acad. Sci. (USA)(1992) 89:5769–5773). The E6 gene is most active in fiber, although low levels of transcripts are found in leaf, ovule and flower.

To obtain a specifically derived transcriptional initiation region, the following steps may be employed. Messenger RNA (mRNA) is isolated from tissue of the desired developmental stage. This mRNA is then used to construct cDNA clones which correspond to the mRNA population both in terms of primary DNA sequence of the clones and in terms of abundance of different clones in the population. mRNA is also isolated from tissue of a different developmental stage in which the target gene should not be expressed (alternate tissue). Radioactive cDNA from the desired tissue and from the alternate tissue is used to screen duplicate copies of the cDNA clones. The preliminary screen allows for classification of the cDNA clones as those which correspond to mRNAs which are abundant in both tissues; those which correspond to mRNAs which are not abundant in either tissue; those which correspond to mRNAs which are abundant in one tissue and relatively non-abundant in the other.

Clones are then selected which correspond to mRNAs that are abundant only in the desired tissue and then these selected clones are further characterized.

Since the hybridization probe for the preliminary screen outlined above is total cDNA from a particular tissue, it hybridizes primarily to the most abundant sequences. In order to determine the actual level of expression, particularly in tissue where the mRNA is not as abundant, the cloned sequence is used as a hybridization probe to the total mRNA population(s) of the desired tissue(s) and various undesired tissue(s). This is most commonly done as a Northern blot which gives information about both the relative abundance of the mRNA in particular tissues and the size of the mRNA transcript.

It is important to know whether the abundance of the mRNA is due to transcription from a single gene or whether it is the product of transcription from a family of genes. This can be determined by probing a genomic Southern blot with the cDNA clone. Total genomic DNA is digested with a variety of restriction enzymes and hybridized with the radioactive CDNA clone. From the pattern and intensity of the hybridization, one can distinguish between the possibilities that the mRNA is encoded either by one or two genes or by a large family of related genes. It can be difficult to determine which of several cross-hybridizing genes encodes the abundantly expressed mRNA found in the desired tissue. For example, tests indicate that pZ130 (see Example 4) is a member of a small gene family however, the pZ7 probe is capable of distinguishing pZ130 from the remainder of the family members.

The cDNA obtained as described can be sequenced to determine the open reading frame (probable protein coding region) and the direction of transcription so that a desired target DNA sequence later can be inserted at the correct site and in the correct orientation into a transcription cassette. Sequence information for the cDNA clone also facilitates characterization of corresponding genomic clones including mapping and subcloning as described below. At the same time, a genomic library can be screened for clones containing the complete gene sequence including the control region flanking the transcribed sequences. Genomic clones generally contain large segments of DNA (approximately 10–20 kb) and can be mapped using restriction enzymes, then subcloned and partially sequenced to determine which segments contain the developmentally regulated gene.

Using the restriction enzyme map and sequence information, plasmids can be designed and constructed which have the putative ovary gene or other desired promoter regions attached to genes which are to be expressed in ovary and/or other desired tissue, particularly ovary-derived tissue. These hybrid constructions are tested for their pattern of expression in transformed, regenerated plants to be sure that the desired timing and/or tissue expression and/or the overall level of expression has been maintained successfully when the promoter is no longer associated with the native open reading frame. Using the method described above, several transcriptional regulatory regions have been identified. One example is the tomato-derived transcriptional initiation region which regulates expression of the sequence corresponding to the pZ130 cDNA clone. Sequences hybridizable to the pZ130 clone, for example, probe pZ7, show abundant mRNA, especially at the early stages of anthesis. The message is expressed in ovary integument and ovary outer pericarp tissue and is not expressed, or at least is not readily detectable, in other tissues or at any other stage of fruit development. Thus, the pZ130 transcriptional initiation region is considered ovary-specific for purposes of this invention. FIG. 1 provides the DNA sequence of CDNA clone pZ130. The native function of the amino acid sequence encoded by the structural gene comprising pZ130 is unknown.

Downstream from, and under the regulatory control of, the ovary tissue transcriptional/translational initiation control region is a nucleotide sequence of interest which provides for modification of the phenotype of structures maturing from ovary tissue, such as fruit or fiber. The nucleotide sequence may be any open reading frame encoding a polypeptide of interest, for example, an enzyme, or a sequence complementary to a genomic sequence, where the genomic sequence may be an open reading frame, an intron, a noncoding leader sequence, or any other sequence where the complementary sequence inhibits transcription, messenger RNA processing, for example, splicing, or translation. The nucleotide sequences of this invention may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest. Phenotypic modification can be achieved by modulating production either of an endogenous transcription or translation product, for example as to the amount, relative distribution, or the like, or an exogenous transcription or translation product, for example to provide for a novel function or products in a transgenic host cell or tissue. Of particular interest are DNA sequences encoding expression products associated with the development of plant fruit, including genes involved in metabolism of cytokinins, auxins, ethylene, abscissic acid, and the like. Methods and compositions for modulating cytokinin expression are described in U.S. Pat. No. 5,177,307, which disclosure is hereby incorporated by reference. Alternatively, various genes, from sources including other eukaryotic or prokaryotic cells, including bacteria, such as those from *Agrobacterium tumefaciens* T-DNA auxin and cytokinin biosynthetic gene products, for example, and mammals, for example interferons, may be used.

Other phenotypic modifications include modification of the color of plant parts developing from ovary integuments and/or core tissue, for example seed coat hairs, such as cotton fibers. Of interest are genes involved in production of melanin and genes involved in the production of indigo. Melanins are dark brown pigments found in animals, plants and microorganisms, any of which may serve as a source for sequences for insertion into the constructs of the present invention. Specific examples include the tyrosinase gene which can be cloned from *Streptomyces antibioticus*. The ORF438 encoded protein in *S. antibioticus* also is necessary for melanin production, and may provide a copper donor function. In addition, a tyrosinase gene can be isolated from any organism which makes melanin. The gene can be isolated from human hair, melanocytes or melanomas, cuttle fish and red roosters, among others. See, for example, EP Application No. 89118346.9 which discloses a process for producing melanins, their precursors and derivatives in microorganisms. Also, See, Bernan et al. Gene (1985) 37:101–110; and della-Cioppa et al. Bio/Technology (1990) 8:634–638.

Indigo may be obtained by use of genes encoding a mono-oxygenase such as xylene oxygenase which oxidizes toluene and xylene to (methyl) benzyl alcohol and also transforms indole to indigo. Cloning of the xylene oxygenase gene and the nucleotide and amino acid sequences are described in unexamined Japanese Patent Application Kokai:2-119777, published May 7, 1990. A dioxygenase such as naphthalene dioxygenase which also converts indole to indigo finds use; the naphthalene dioxygenase gene nahA is described in Science (1983) 222:167. For cloning, nucleotide sequence in characterization of genes encoding naphthalene dioxygenase of Pseudomonas putida. See, Kurkela et al. Gene (1988) 73:355–362. A tryptophanase gene sequence can be used in conjunction with an oxygenase to increase the amount of indole available for conversion to indigo. Sources of tryptophanase gene sequences include E. coli (see, for example, Deeley et al. (1982) J. Bacteriol. 151:942–951).

As demonstrated in the following examples, expression of ORF438 and tyrosinase genes from Streptomyces in transgenic tobacco plants using a pZ7 promoter, and targeting the gene products to plastids by the action of transit peptides resulted in phenotypic modification of tissues ovary and meristem derived tissues, including modification of color in meristematic regions and basal flower buds. A similar set of experiments in which no plastid targeting sequences were used in conjunction with the ORF438 and tyrosinase genes, no alteration of phenotype was observed. Presumably, the plants were not able to produce melanin due to deficiency of the required substrates in the plant cell cytosol. Plastid targeting sequences (transit peptides) are available from a number of plant nuclear-encoded plastid proteins, such as the small subunit (SSU) of ribulose bisphosphate carboxylase, plant fatty acid biosynthesis related genes including acyl carrier protein (ACP), stearoyl-ACP desaturase, β-ketoacyl-ACP synthase and acyl-ACP thioesterase, or LHCPII genes. The encoding sequence for a transit peptide which provides for transport to plastids may include all or a portion of the encoding sequence for a particular transit peptide, and may also contain portions of the mature protein encoding sequence associated with a particular transit peptide. There are numerous examples in the art of transit peptides which may be used to deliver a target protein into a plastid organelle. The particular transit peptide encoding sequence used in the instant invention is not critical, as long as delivery to the plastid is obtained.

As an alternative to using transit peptides to target pigment synthesis proteins to plastid organelles, the desired constructs may be used to transform the plastid genome directly. In this instance, promoters capable of providing for transcription of genes in plant plastids are desired. Of particular interest is the use of a T7 promoter to provide for high levels of transcription. Since plastids do not contain an appropriate polymerase for transcription from the T7 promoter, T7 polymerase may be expressed from a nuclear construct and targeted to plastids using transit peptides as described above. (See McBride et al. (1994) Proc. Nat. Acad. Sci. 91:7301–7305; see also U.S. Pat. No. 5,925,806 entitled "Controlled Expression of Transgenic Constructs in Plant Plastids", and U.S. Pat. No. 5,576,198 and PCT/US94/14574 filed Dec. 12, 1994.) Tissue specific or developmentally regulated promoters may be useful for expression of the T7 polymerase in order to limit expression to the appropriate tissue or stage of development. For example, for flower color modification, the T7 polymerase may be expressed from a petal specific promoter to limit effects to the desired tissue.

Targeting of melanin synthesis genes to vacuoles is also of interest in plant tissues which accumulate the tyrosine substrate involved in melanin synthesis in vacuoles. The protein signal for targeting to vacuoles may be provided from a plant gene which is normally transported across the rough endoplasmic reticulum, such as the 32 amino acid N-terminal region of the metallocarboxypeptidase inhibitor gene from tomato (Martineau et al. (1991) Mol. Gen. Genet. 228:281–286). In addition to the signal sequence, vacuolar targeting constructs also encode a vacuolar localization signal (VLS) positioned at the carboxy terminus of the encoded protein. Appropriate signal sequences and VLS regions may be obtained from various other plant genes and may be similarly used in the constructs of this invention. Numerous vacuolar targetting peptides are known to the art, as are reviewed in Chrispeels et al., Cell (1992) 68:613–616.

Thus, it is recognized that constructs of the instant invention which provide sequences encoding genes involved in color production and sequences which provide for targeting of the gene products to appropriate cellular locations have broad application to modification of color in various plant tissues. Plant transcriptional initiation regions for use with these color modification constructs will depend upon the particular plant tissue to be modified. For cotton fiber modification, for example, cotton fiber specific promoters or the pZ7 promoter described herein may find use. Additional cotton fiber promoters which may find use in the methods of the instant application are described in copending US patent application to Pear et al., entitled "Cotton Fiber Transcriptional Factors", Ser. No. 08/480,178, filed on Jun. 7, 1995. For flower color modification, promoters from genes preferentially expressed in flowers, and particularly in flower petals, are of interest. Examples of promoters useful for expression in flowers include chalcone synthase, as described in Holton et al. (1994) TIBTECH, Vol 12, pages 40–42(see also Napoli et al. (1990) Plant Cell, Vol 2, pages 79–89; Lipphardt et al., (1988) EMBO, 7(13) pages 4027–4034; and Toguri et al., (1993) Plant Mol Biol, Vol 23, pages 933–946).

Also of interest are genes involved in production of colored pigments in plant tissues, such as the Maize A1 gene which encodes a dihydroflavonol reductase, an enzyme of the anthocyanin pigmentation pathway. In cells that express the A1 gene, dihydrokempferol is converted to 2–8 alkylleucopelargonidin, which may be further metabolized to pelargonidin pigment by endogenous plant enzymes. Other anthocyanin or flavonoid type pigments may also be of interest for modification of cotton cell fibers, plant flowers or other plant tissues. For a review of plant flower color, see van Tunen et al. (in Plant Biotechnology Series, Volume 2 (1990) Developmental Regulation of Plant Gene Expression, D. Grierson ed.).

Although cotton fibers in commercially grown varieties are primarily white in color, other naturally occurring cotton varieties have brown or reddish-brown fibers. Also a cotton line containing green colored fibers has been identified. The existence of these colored cotton lines suggests that the precursors required for the anthocyanin pigment pathways are present in cotton fibers cells, thus allowing further color phenotype modifications.

For some applications, it is of interest to modify other aspects of structures developing from the ovary integument and related structures. For example, it is of interest to modify various aspects of cotton fibers, such as strength or texture of a fiber. Thus, the appropriate gene may be inserted in the constructs of the invention, including genes for PHB biosynthesis (see, Peoples et al. J. Biol. Chem. (1989) 264:15298–15303 and Ibid. 15293–15397; Saxena, Plant Molecular Biology (1990) 15:673–683, which discloses cloning and sequencing of the cellulose synthase catalytic subunit gene; and Bowen et al. PNAS (1992) 89:519–523) which discloses chitin synthase genes of Saccharomyces cerevisiae and Candida albicans.

Transcriptional cassettes may be used when the transcription of an anti-sense sequence is desired. When the expression of a polypeptide is desired, expression cassettes providing for transcription and translation of the DNA sequence of interest will be used. Various changes are of interest; these changes may include modulation (increase or decrease) of formation of particular saccharides, hormones, enzymes, or other biological parameters. These also include modifying the composition of the final fruit or fiber, that is changing the ratio and/or amounts of water, solids, fiber or sugars. Other phenotypic properties of interest for modification include response to stress, organisms, herbicides, brushing, growth regulators, and the like. These results can be achieved by providing for reduction of expression of one or more endogenous products, particularly an enzyme or cofactor, either by producing a transcription product which is complementary (anti-sense) to the transcription product of a native gene, so as to inhibit the maturation and/or expression of the transcription product, or by providing for expression of a gene, either endogenous or exogenous, to be associated with the development of a plant fruit.

The termination region which is employed in the expression cassette will be primarily one of convenience, since the termination regions appear to be relatively interchangeable. The termination region may be native with the transcriptional initiation region, may be native with the DNA sequence of interest, may be derived from another source.

The termination region may be naturally occurring, or wholly or partially synthetic. Convenient termination regions are available from the Ti-plasmid of A. tumefaciens, such as the octopine synthase and nopaline synthase termination regions. In some embodiments, it may be desired to use the 3' termination region native to the ovary tissue transcription initiation region used in a particular construct.

As described herein, in some instances additional nucleotide sequences will be present in the constructs to provide for targeting of a particular gene product to specific cellular locations. For example, where coding sequences for synthesis of aromatic colored pigments are used in a construct, particularly coding sequences for enzymes which have as their substrates aromatic compounds such tyrosine and indole, it is preferable to include sequences which provide for delivery of the enzyme into plastids, such as an SSU transit peptide sequence. Also, for synthesis of pigments derived from tyrosine, such as melanin, targeting to the vacuole may provide for enhanced color modifications.

For melanin production, the tyrosinase and ORF438 genes from *Streptomyces antibioticus* (Berman et al. (1985) 37:101–110) are provided in cotton fiber cells for expression from a pZ130 promoter. In Streptomyces, the ORF438 and tyrosinase proteins are expressed from the same promoter region. For expression from constructs in a transgenic plant genome, the coding regions may be provided under the regulatory control of separate promoter regions. The promoter regions may be the same or different for the two genes. Alternatively, coordinate expression of the two genes from a single plant promoter may be desired. Constructs for expression of the tyrosinase and ORF438 gene products from pZ130 promoter regions are described in detail in the following examples. Additional promoters may also be desired, for example plant viral promoters, such as CaMV 35S, can be used for constitutive expression of one of the desired gene products, with the other gene product being expressed in cotton fiber tissues from the pZ130 promoter. In addition, the use of other plant promoters for expression of genes in cotton fibers is also considered, such as the Brassica seed promoters and the E6 gene promoter discussed above. Similarly, other constitutive promoters may also be useful in certain applications, for example the mas, Mac or DoubleMac, promoters described in U.S. Pat. No. 5,106,739 and by Comai et al., *Plant Mol. Biol.* (1990) 15:373–381). When plants comprising multiple gene constructs are desired, for example plants expressing the melanin genes, ORF438 and tyrosinase, the plants may be obtained by co-transformation with both constructs, or by transformation with individual constructs followed by plant breeding methods to obtain plants expressing both of the desired genes.

The various constructs normally will be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which has been introduced. Components of DNA constructs including transcription cassettes of this invention may be prepared from sequences which are native (endogenous) or foreign (exogenous) to the host. By foreign is intended that the sequence is not found in the wild-type host into which the construct is introduced. Heterologous constructs will contain at least one region which is not native to the gene from which the ovary tissue transcription initiation region is derived.

In preparing the constructs, the various DNA fragments may be manipulated, so as to provide for DNA sequences in the proper orientation and, as appropriate, in proper reading frame for expression; adapters or linkers may be employed for joining the DNA fragments or other manipulations may be involved to provide for convenient restriction sites, removal of superfluous DNA, removal of restriction sites, or the like. In vitro mutagenesis, primer repair, restriction, annealing, resection, ligation, or the like may be employed, where insertions, deletions or substitutions, e.g. transitions and transversions, may be involved. Conveniently, a vector or cassette may include a multiple cloning site downstream from the ovary-related transcription initiation region, so that the construct may be employed for a variety of sequences in an efficient manner.

In carrying out the various steps, cloning is employed, so as to amplify the amount of DNA and to allow for analyzing the DNA to ensure that the operations have occurred in proper manner. By appropriate manipulations, such as restriction, chewing back or filling in overhangs to provide blunt ends, ligation of linkers, or the like, complementary ends of the fragments can be provided for joining and ligation. A wide variety of cloning vectors are available, where the cloning vector includes a replication system functional in *E. coli* and a marker which allows for selection of the transformed cell. Illustrative vectors include pBR332, pUC series, M13mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence. Each of the partial constructs may be cloned in the same or different plasmids.

A variety of techniques are available and known to those skilled in the art for introduction of constructs into a plant cell host. These techniques include transfection with DNA employing *A. tumefaciens* or *A. rhizogenes* as the transfecting agent, protoplast fusion, injection, electroporation, particle acceleration, etc. For transformation with Agrobacterium, plasmids can be prepared in *E. coli* which contain DNA homologous with the Ti-plasmid, particularly T-DNA. The plasmid may or may not be capable of replication in Agrobacterium, that is, it may or may not have a broad spectrum prokaryotic replication system such as does, for example, pRK290, depending in part upon whether the transcription cassette is to be integrated into the Ti-plasmid or to be retained on an independent plasmid. The Agrobacterium host will contain a plasmid having the vir genes necessary for transfer of the T-DNA to the plant cell and may or may not have the complete T-DNA. At least the right border and frequently both the right and left borders of the T-DNA of the Ti- or Ri-plasmids will be joined as flanking regions to the transcription construct. The use of T-DNA for transformation of plant cells has received extensive study and is amply described in EPA Ser. No. 120,516, Hoekema, In: The Binary Plant Vector System Offset-drukkerij Kanters B.V., Alblasserdam, 1985, Chapter V, Knauf, et al., Genetic Analysis of Host Range Expression by Agrobacterium, In: Molecular Genetics of the Bacteria-Plant Interaction, Puhler, A. ed., Springer-Verlag, NY, 1983, p. 245, and An, et al., *EMBO J.* (1985) 4:277–284.

For infection, particle acceleration and electroporation, a disarmed Ti-plasmid lacking particularly the tumor genes found in the T-DNA region may be introduced into the plant cell. By means of a helper plasmid, the construct may be transferred to the *A. tumefaciens* and the resulting transfected organism used for transfecting a plant cell; explants may be cultivated with transformed *A. tumefaciens* or *A. rhizogenes* to allow for transfer of the transcription cassette to the plant cells. Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated. Transgenic plant cells are then placed in an appropriate selective medium for selection of transgenic cells which are then grown to callus, shoots grown and plantlets generated from the shoot by growing in rooting medium.

To confirm the presence of the transgenes in transgenic cells and plants, a Southern blot analysis can be performed using methods known to those skilled in the art. Expression products of the transgenes can be detected in any of a variety of ways, depending upon the nature of the product, and include immune assay, enzyme assay or visual inspection, for example to detect pigment formation in the appropriate plant part or cells. Once transgenic plants have been obtained, they may be grown to produce fruit having the desired phenotype. The fruit or fruit parts, such as cotton fibers may be harvested, and/or the seed collected. The seed may serve as a source for growing additional plants having the desired characteristics. The terms transgenic plants and transgenic cells include plants and cells derived from either transgenic plants or transgenic cells.

The various sequences provided herein may be used as molecular probes for the isolation of other sequences which may be useful in the present invention, for example, to obtain related transcriptional initiation regions from the same or different plant sources. Related transcriptional initiation regions obtainable from the sequences provided in this invention will show at least about 60% homology, and more preferred regions will demonstrate an even greater percentage of homology with the probes. Of particular importance is the ability to obtain related transcription initiation control regions having the timing and tissue parameters described herein. For example, using the probe pZ130, at least 7 additional clones, have been identified, but not further characterized. Thus, by employing the techniques described in this application, and other techniques known in the art (such as Maniatis, et al., *Molecular Cloning, —A Laboratory Manual* (Cold Spring Harbor, N.Y.) 1982), other transcription initiation regions capable of directing ovary tissue transcription as described in this invention may be determined. The constructs can also be used in conjunction with plant regeneration systems to obtain plant cells and plants; the constructs may also be used to modify the phenotype of a fruit and fruits produced thereby.

For flower color modification, transformation of various flowering plant species is desired, including transformation of carnations, roses, gerba, lillies, orchids, petunias and chrysanthemums. For cotton applications, various varieties and lines of cotton may find use in the described methods. Cultivated cotton species include *Gossypium hirsutum* and *G. babadense* (extra-long stable, or Pima cotton), which evolved in the New World, and the Old World crops *G. herbaceum* and *G. arboreum*. The following examples are offered by way of illustration and not by limitation.

EXPERIMENTAL

The following deposits have been made at the American Type Culture Collection (ATCC) (12301 Parklawn Drive, Rockville, Md. 20852). Bacteriophage Calgene Lambda 116 and Calgene Lambda 140, each containing a transcription initiation region of this invention, were deposited on Jul. 13, 1989 and were given accession numbers 40632 and 40631, respectively.

EXAMPLE 1

Construction of Pre-Anthesis Tomato Ovary cDNA Banks and Screening for Ovary-Specific Clones cDNA Library Preparation Tomato plants (*Lycopersicon esculentum* cv UC82B) were grown under greenhouse conditions. Poly(A)+RNA was isolated as described by Mansson et al., *Mol. Gen. Genet.* (1985) 200:356–361. The synthesis of cDNA from poly(A)+RNA, prepared from ovaries of unopened tomato flowers (pre-anthesis stage), was carried out using the BRL cDNA Cloning Kit following the manufacturer's instructions (BRL; Bethesda, Md.). Addition of restriction endonuclease EcoRI linkers (1078, New England Biolabs; Beverly, Mass.) to the resulting double-stranded cDNA was accomplished by using the procedures described in Chapter 2 of *DNA Cloning Vol. I: A Practical Approach*, Glover, ed., (BRL Press, Oxford 1985). Cloning the cDNA into the EcoRI site of the phage Lambda ZAP (Stratagene; La Jolla, Calif.) and packaging the resulting recombinant phage (using GigaPack Gold, Stratagene) was carried out as described in the respective commercial protocols.

Two cDNA libraries were prepared as described above from the same pre-anthesis stage mRNA. For the second library, which contained significantly longer cDNA than the first, the poly(A)+RNA sample was run through an RNA spin column (Boehringer Mannheim Biochemicals; Indianapolis, Ind.), following the manufacturer's directions, prior to the cloning procedures.

cDNA Library Screening

The first cDNA library was screened by differential hybridization using $^{32}$P-labeled CDNA probes made from pre-anthesis mRNA, leaf mRNA and young seedling mRNA. Clones were selected based on hybridization to only pre-anthesis mRNA. The cDNAs corresponding to the selected Lambda ZAP (Stratagene) clones were excised from the phage vector and propagated as plasmids (following the manufacturer's instructions).

From an initial screen of 1000 cDNAs, 30 selected clones falling into five classes based on the sequences of their cDNA inserts were isolated. Two clones, clones pZ7 and pZ8, were selected for further study. The DNA sequences of pZ7 and pZ8 are shown as the underlined portions of FIGS. 1 and 4, respectively.

Several thousand recombinant clones from the second cDNA library were screened by plaque hybridization (as described in the Stratagene Cloning Kit Instruction Manual) with a mixture of radiolabeled DNA probes. Screening of approximately three thousand recombinant clones from the second library with the pZ7 and pZ8 DNA probes yielded selection of fourteen clones which had intense hybridization signals. The clones selected were excised from the phage vector and propagated as plasmids. DNA was isolated from each clone, cut with the restriction endonuclease EcoRI, then electrophoresed through a 0.7% agarose gel. Duplicate blot hybridizations were performed as described in Maniatis et al., *Molecular Cloning: A Laboratory Manual* (Cold Spring Harbor, N.Y., 1982) with radiolabeled probes representing the genes of interest (pZ7 and pZ8). Seven clones which hybridized to pZ7 and three clones which hybridized to pZ8 were selected. The longest of these for each probe, pZ130 (pZ7-hybridizing) and pZ70 (pZ8-hybridizing), were characterized further and used in additional experiments.

EXAMPLE 2

Analysis of cDNA Clones

Northern Analysis

Tissue-specificity of the cDNA clones was demonstrated as follows: RNA was isolated from 1, 2, 3, 4, 5, 6, 7, 10, 14, 17 and 21 day post-anthesis, anthesis and pre-anthesis stage tomato ovaries, tomato leaves and unorganized tomato callus using the method of Ecker and Davis, *Proc. Natl. Acad. Sci. USA*, 84:5203 (1987) with the following modifications. After the first precipitation of the nucleic acid, the pellets were resuspended in 2 ml of diethylpyrocarbonate (DEP) treated water on ice. The solutions were brought to 1 mM MgC12 and ¼ volume of 8 M LiCl was added. The samples were mixed well and stored at 4° C. overnight. The samples were then centrifuged at 8,000 RPM for 20 min. at 4° C. The pellets were dried, resuspended in DEP-treated water on ice as before and ethanol-precipitated once more. The RNAs were electrophoresed on formaldehyde/agarose gels according to the method described by Fourney et al., *Focus* (1988) 10:5–7, immobilized on Nytran membranes (Schleicher & Schuell; Keene, N. H.) and hybridized with $^{32}$P-labeled probes.

Based upon the Northern analysis with a $^{32}$P-labeled pZ7 EcoRI insert DNA or a pZ8 EcoRI insert DNA, it is clear that both of these genes are most highly expressed at anthesis in tomato variety UC82B and somewhat less highly expressed prior to and a day following the opening of the flower. FIG. 6 shows tomato flowers at various stages of development and immediately below, a representative ovary dissected from a flower at the same stage of development. As seen in FIG. 6, by two days after the onset of anthesis, the expression of both genes had dropped off dramatically. The size of the mRNA species hybridizing to the pZ7 probe was approximately 800 nt and to the pZ8 probe approximately 500 nt.

From two days post-anthesis, pZ8 RNA accumulation was apparently maintained at a relatively low level while pZ7 RNA accumulation continued to drop off steadily until, by three weeks post-anthesis, it was undetectable by this analysis. pZ8 RNA accumulation was not detectable by the method described above in RNA samples isolated from tomato fruit older than the immature green stage of fruit ripening. No RNA hybridizing to pZ7 or pZ8 was found in callus tissue; no RNA hybridizing to pZ7 was found in leaf tissue; on longer exposures a barely detectable hybridization signal for pZ8 was seen in leaf RNA.

Expression Level

Message abundance corresponding to the cDNA probes was determined by comparing the hybridization intensity of a known amount of RNA synthesized in vitro from the clones (using T7 or T3 RNA polymerase in the Riboprobe System (Promega)) to RNA from anthesis stage and three week old tomato ovaries. This analysis indicated that pZ7 and pZ8 cDNAs represent abundant RNA classes in anthesis-stage tomato ovaries, being approximately 5% and 2% of the message, respectively.

Cellular Specificity

The cellular specificity of the cDNA probes may be demonstrated using the technique of in situ hybridization. Pre-anthesis stage UC82B tomato ovaries were fixed overnight in a 4% paraformaldehyde, phosphate buffered saline (PBS), 5 MM $MgCl_2$ solution, pH 7.4 (PBS is 10 mM phosphate buffer, pH 7.4, 150 mM NaCl) (Singer et al., *Biotechniques* (1986) 4:230–250). After fixation, the tissue was passed through a graded tertiary butyl alcohol (TBA) series, starting at 50% alcohol, infiltrated with Paraplast and cast into paraffin blocks for sectioning (Berlyn and Miksche, *Botanical Microtechnique and Cytochemistry,* (1976) Iowa). Embedded ovaries were transversely cut, 8 $\mu$m thick sections, on a Reichert Histostat rotary microtome. Paraffin ribbons holding 5–7 ovary sections were affixed to gelatin-chrom alum subbed slides (Berlyn and Miksche (1976) supra) and held in a dust-free box until in situ hybridizations were performed. Slides ready to be hybridized were deparaffinized in xylene and rehydrated by passing through an ethanol hydration series as described in Singer et al., supra (1986).

A 2× hybridization mix was made consisting of 100 $\mu$l 20×SSC, 20 $\mu$l 10% BSA, 100 $\mu$l 750 mM DTT, 200 $\mu$l 50% dextran sulfate, 50 $\mu$l RNasin, and 30 $\mu$l sterile water. Sense and antisense $^{35}$S-RNA probes were generated from cDNAs of interest using T3 and T7 RNA polymerases in vitro transcription (Riboprobe Promega Biotec or Stratagene) reactions following the manufacturer's protocol. 2.5 $\mu$l tRNA (20 mg/ml), 2.5 $\mu$l salmon sperm DNA (10 mg per ml) and 4×10$^6$ cpm/ probe were dried down using a lyophilizer. This mix was then resuspended in 25 $\mu$l 90% formamide containing 25 $\mu$l 2× hybridization mix per slide. 40 $\mu$l of this hybridization mix was placed on each slide. A cover slip was placed over the sections and edges sealed with rubber cement. Slides were placed in slide holders inside a glass slide box, covered, and placed in a 37° C. dry oven overnight to hybridize. Posthybridization treatments were as described in Singer et al., (1986), supra.

Autoradiography was performed as described in *KODAK Materials for Light Microscope* (KODAK (1986); Rochester, N.Y.) using liquid emulsion NTB-3. Slides are left to expose in a light-tight box for approximately two weeks. After developing the autoradiographic slides, sections were stained in 0.05% toluidine blue and then dehydrated through a graded alcohol series; xylene:100% ethanol, 1:1, followed by 2 changes of 100% xylene, five minutes in each solution. Coverslips were mounted with Cytoseal (VWR; San Francisco, Calif.) and left on a slide warmer until dry (45–50° C., 1–2 days). Autoradiographic slides were then ready for microscopic examination.

When pre-anthesis tomato ovaries were hybridized to sense and antisense 35S-pZ7 RNA, the antisense transcripts hybridized specifically to the outer pericarp region of the ovary and to the outer region of the ovules (the integuments). The sense transcripts (negative control) showed no hybridization. When pre-anthesis tomato ovaries were hybridized to sense and antisense 35S-pZ8 RNA, the antisense transcript hybridized specifically to the inner core region of the ovary and to the outer region of the ovules. The sense transcripts showed no hybridization.

In summary, the mRNA transcripts encoded by the genes corresponding to pZ7 and pZ8 were abundantly expressed during a very specific stage of tomato fruit development, primarily at anthesis and at a day prior to and after the opening of the flower. The transcripts additionally were expressed in a specific subset of tomato ovary cell types during that stage of development particularly in the integuments (pZ7 and pZ8) as well as the ovarian outer pericarp (pZ7) and inner core region (pZ8).

EXAMPLE 3

Sequencing of DZ130 and pZ70 cDNA Clones

The complete DNA sequences of the cDNA pZ130 and pZ70 clones were determined using the Sanger et al. (1971) dideoxy technique. The DNA sequences of both pZ130 and pZ70 were translated in three frames. The sequences, including the longest open reading frame for each, are shown in FIG. 1 (pZ130) and FIG. 4 (pZ70).

EXAMPLE 4

Analysis of Gene Family

Southern analysis was performed as described by Maniatis et al., supra, (1982). Total tomato DNA from cultivar UC82B was digested with BamHI, EcoRI and HindIII, separated by agarose gel electrophoresis and transferred to nitrocellulose. Southern hybridization was performed using $^{32}$P-labeled probes produced by random priming of pZ130 or pZ70. A simple hybridization pattern indicated that the genes encoding pZ130 and pZ70 are present in a few or perhaps only one copy in the tomato genome.

Additional analysis, using a pZ130 hybridization probe to hybridize to tomato genomic DNA digested with the restriction endonuclease BglII, indicated that this gene is actually a member of a small (approximately 5–7 member) family of genes. The original pZ7 CDNA clone, consisting of sequences restricted to the 3' untranslated region of the longer pZ130 clone, however, hybridizes intensely only to one band and perhaps faintly to a second band based on Southern analysis using BglII digested tomato genomic DNA.

EXAMPLE 5

Preparation of Genomic Clones DZ130 and pZ70

Two genomic clones, one representing each of cDNA clones pZ130 and pZ70, were obtained as follows. A genomic library constructed from DNA of the tomato cultivar UC82B, partially digested with the restriction endonuclease Sau3A, was established in the lambda phage vector, lambda-FIX according to the manufacturer's instructions (Stratagene; La Jolla, Calif.). This library was screened using $^{32}$P-labeled pZ130 and pZ70 as probes. A genomic clone containing approximately 14.5 kb of sequence from the tomato genome which hybridized to pZ70 was isolated. The region which hybridizes to the pZ70 probe was found within the approximately 2 kb XbaI-HindIII restriction fragment of Calgene Lambda 116 (See FIG. 5). A second genomic clone, containing approximately 13 kb of sequence from the tomato genome and hybridizing to pZ130 (and pZ7) was isolated. The region which hybridized to the pZ130 probe was found within the larger EcoRI-HindIII restriction fragment of Calgene Lambda 140 (See FIG. 3).

Preparation of pCGN2015 pCGN2015 was prepared by digesting pCGN565 with HhaI, blunting with mung bean nuclease, and inserting the resulting fragment into an EcoRV digested BluescriptKSM13-(Stratagene) vector to create pCGN2008. pCGN2008 was digested with EcoRI and HindIII, blunted with Klenow, and the 1156 bp chloramphenicol fragment isolated. BluescriptKSM13+ (Stratagene) was digested with DraI and the 2273 bp fragment isolated and ligated with the pCGN2008 chloramphenicol fragment creating pCGN2015.

Preparation of pCGN2901/pCGN2902 pCGN2901 contains the region surrounding the pZ7-hybridizing region of the pZ130 genomic clone, including approximately 1.8 kb in the 5' direction and approximately 4 kb in the 3'-direction. To prepare pCGN2901, Calgene Lambda 140 was digested with SalI and the resulting fragment which contains the pZ7-hybridizing region was inserted into pCGN2015, at the pCGN2015 unique SalI site, to create pCGN2901.

pCGN2902 contains the other SalI fragment (non-pZ7-hybridizing) of the pZ130 genome derived from SalI digestion of Calgene Lambda 140, also put into a pCGN2015 construct.

EXAMPLE 6

Preparation of a pZ130 Expression Construct

Plasmid DNA isolated from pCGN2901 was digested to completion with NcoI and then treated with exonuclease isolated from mung bean (Promega, Madison, Wis.) to eliminate single-stranded DNA sequences including the ATG sequence making up a portion of the NcoI recognition sequence. The sample was then digested to completion with SacI. The resulting 1.8 kb (approximate) 5' SacI to NcoI fragment was then inserted into a pUC-derived ampicillin-resistant plasmid, pCGP261 (described below), that had been prepared as follows. pCGP261 was digested to completion with XbaI, the single-stranded DNA sequences were filled in by treatment with the Klenow fragment of DNA polymerase I, and the pCGP261 DNA redigested with SacI. The resulting expression construct contained, in the 5' to 3' direction of transcription, an ovary tissue promoter derived from Lambda 140, a tmr gene and tmr 3'-transcriptional termination region.

The plasmid pCGP261 contains the sequences from position 8,762 through 9,836 from the *Agrobacterium tumefaciens* octopine Ti plasmid pTi15955 (as sequenced by Barker et al., *Plant Molec. Biol.* (1983) 2:335–350). This region contains the entire coding region for the genetic locus designated tmr which encodes isopentenyltransferase (Akiyoshi et al., *PNAS* (1984) 81:4776–4780), 8 bp 5' of the translation initiation ATG codon and 341 bp of sequences 3' to the translation stop TAG codon.

Plasmid pCGP261 was created as follows. Plasmid pCGN1278 (described in co-pending application U.S. Ser. No. 07/382,176, filed Jul. 19, 1989, which is hereby incorporated in its entirety by reference) was digested with XbaI and EcoRI. The single-stranded DNA sequences produced were filled in by treatment with the Klenow fragment of DNA polymerase I. The XbaI to EcoRI fragment containing the tmr gene was then ligated into the vector ml3 Bluescript minus (Stratagene Inc., La Jolla, Calif.) at the SmaI site, resulting in plasmid pCGP259. All of the region found upstream of the ATG translation initiation codon and some of the tmr gene coding region was eliminated by digesting pCGP259 with BspMI and BstXI. The resulting coding region and 8 bp of the sequence originally found upstream of the first ATG codon was re-introduced into the plasmid and an XbaI site introduced into the plasmid via a synthetic oligonucleotide comprising the following sequence (SEQ ID NO. 4): 5' AATTAGATGCAGGTCCAT-AAGTTTTTTCTAGACGCG 3'. The resulting plasmid is pCGP261. An XbaI to KpnI fragment of pCGP261 containing the pZ130 gene 5' and tmr gene coding and 3' region construct was then inserted into a binary cassette such as pCGN1557 and transgenic plants prepared. (See co-pending application U.S. Ser. No., 07/382,176 described above).

EXAMPLE 7

Preparation of pZ130 Promoter Cassette

The pZ130 cassette contains 1.8 kb (pCGN2909) or 5 kb (pCGN2928) of DNA 5' of the translational start site and the 3' region (from the TAA stop codon to a site 1.2 kb downstream) of the pZ130 gene. The pZ130 cassettes were constructed as follows.

Transcriptional Initiation Region

Plasmid DNA isolated from pCGN2901 (see above) was digested to completion with NcoI and then treated with exonuclease isolated from mung bean (Promega, Madison, Wis.) to eliminate single-stranded DNA sequences, including the ATG sequence making up a portion of the NcoI recognition sequence. The sample was then digested to completion with SacI. The resulting 1.8 kb 5' SacI to NcoI fragment was then inserted into pCGN2015 (described above) to create pCGN2904.

In order to eliminate redundant restriction enzyme sites and make subsequent cloning easier, plasmid DNA isolated from pCGN2904 was digested to completion with SalI and EcoRI and the resulting 1.8 kb fragment, containing the pZ130 5' sequences, inserted into pBluescriptII (Stratagene; La Jolla, Calif.) to create pCGN2907.

Transcriptional and Translational Termination Region

Plasmid DNA isolated from pCGN2901 was digested to completion with EcoRI and BamHI. The resulting 0.72 kb EcoRI to BamHI fragment located downstream (3') from the pZ130 coding region was inserted into pCGN2907 creating pCGN2908.

The insertion of the 0.5 kb (approximately) DNA sequence, including the pZ130 gene TAA stop codon and those sequences between the stop codon and the EcoRI site downstream (3') and the addition of unique restriction sites to facilitate insertion of foreign genes, was accomplished as follows.

A polylinker/"primer" comprising the sequence (SEQ ID NO. 5) 5'GTTCCTGCAGCATGCCCGGGATC-GATAATAATTA AGTGAGGC-3' was synthesized to create a polylinker with the following sites: PstI-SphI-SmaI-ClaI and to include the pZ130 gene TAA stop codon and the following (3') 13 base pairs of the pZ130 gene 3' region sequence. Another oligonucleotide comprising the sequence (SEQ ID NO. 6) 5'-CAAGAATTCATAATATTATATATAC-3' was synthesized to create a "primer" with an EcoRI restriction site and 16 base pairs of the pZ130 gene 3' region immediately adjacent to the EcoRI site located approximately 0.5 kb 3' of the pZ130 gene TAA stop codon.

These synthetic oligonucleotides were used in a polymerase chain reaction (PCR) in which plasmid DNA isolated from pCGN2901 was used as the substrate in a thermal cycler (Perkin-Elmer/Cetus, Norwalk, Conn.) as per the manufacturer's instructions. The resulting 0.5 kb DNA product was digested to completion with PstI and EcoRI and the resulting 0.5 kb DNA fragment inserted into pCGN2908 to create pCGN2909. The complete DNA sequence of the 0.5 kb region from the PstI site to the EcoRI site was determined using the Sanger et al. (1971) dideoxy technique to verify that no mistakes in the sequence had occurred between the oligonucleotide primers during the PCR reaction.

The pZ130 cassette, pCGN2909, thus comprises the 5' pZ130 DNA sequences from the SalI site at position 808 to position 2636 (see FIG. 2), unique PstI, SphI and SmaI sites which can be conveniently used to insert genes, and the 3' pZ130 DNA sequences from the TAA stop codon at position 3173 (FIG. 2) through the BamHI site at position 4380.

EXAMPLE 8

Preparation and Analysis of Test Constructs

A β-glucuronidase (GUS) reporter gene was used to evaluate the expression and tissue specificity of the pZ130-GUS constructions. GUS is a useful reporter gene in plant systems because it produces a highly stable enzyme, there is little or no background (endogenous) enzyme activity in plant tissues, and the enzyme is easily assayed using fluorescent or spectrophotometric substrates. (See, for example, Jefferson, *Plant Mol. Rep.* (1987) 5:387–405.) Histochemical stains for GUS enzyme activity are also available which can be used to analyze the pattern of enzyme accumulation in transgenic plants. Jefferson (1987), supra.

A pZ130 cassette, pCGN2928, was prepared by inserting the 3.2 KpnI to SalI fragment of pCGN2059 into the KpnI and SalI sites of pCGN2909. pCGN2059 was prepared by inserting the 3.2 SalI to BglII fragment of pCGN2902 into M13mp19. pCGN2928 is thus identical to pCGN2909 except that it includes an additional approximately 3.2 kb of pZ130 DNA sequence upstream of the SalI site located at position 808 of FIG. 2.

Preparation of Test Constructs pCGN2917 and pCGN2918

These constructs contain 1.8 kb of pZ130 5' sequence, the GUS gene coding region and 1.2 kb of pZ130 3' sequence. pCGN2917 and pCGN2918 differ from each other only in the orientation of the pZ130/GUS construction with respect to the other elements of the binary vector plasmid for example, the 35S promoter from CaMV.

The constructs were made by inserting the PstI fragment of pRAJ250 (Jefferson (1987) supra), or any other plasmid construct having the PstI fragment containing the GUS coding region, into the PstI site of pCGN2909. The resulting plasmid, having the GUS gene in the sense orientation with respect to the pZ130 gene promoter region, was named pCGN2914. The pZ130/GUS construction was excised as an XbaI to KpnI fragment and cloned into the binary vectors pCGN1557 and pCGN1558 to make pCGN2917 and pCGN2918, respectively. pCGN1557 and pCGN1558 are described in McBride and Summerfelt, *Plant Mol. Bio.* (1990) 14:269–296.

Preparation of Test Construct pCGN2926

This construct contains S kb of pZ130 5' sequence, the GUS gene coding region and 1.2 kb of pZ130 3' sequence. It was made by inserting the 3.2 kb KpnI to SalI fragment of pCGN2059 into the KpnI and SalI sites of pCGN2914. The resulting plasmid was named pCGN2923. The pZ130/GUS/pZ130 construction was then excised from pCGN2923 as an XbaI to KpnI fragment and cloned into the binary vector pCGN1557 resulting in pCGN2926.

Analysis of GUS Enzyme Activity

β-glucuronidase activity of transformants was measured using 4-methyl-umbelliferyl glucuronide as a substrate, as outlined in Jefferson (1987) supra GUS enzyme activity was easily detected in the ovaries of the transformed plants and quantitatively was quite high in comparison with the activity background observed in ovaries isolated from nontransformed tomato plants and from leaves of transformed plants. Interestingly, upon comparison of the pCGN2917 and pCGN2918 transformants, it was found that proximity to a 35S CaMV enhancer region (pCGN1558) may reduce, or eliminate, ovary-tissue specificity.

EXAMPLE 9

PZ-7 Cotton Transformation

Explant Preparation

Coker 315 seeds were surface disinfected by placing in 50% Clorox (2.5% sodium hypochlorite solution) for 20 minutes and rinsing 3 times in sterile distilled water. Following surface sterilization, seeds were germinated in 25×150 sterile tubes containing 25 mls ½×MS salts: ½×B5 vitamins: 1.5% glucose: 0.3% gelrite. Seedlings were germinated in the dark at 28° C. for 7 days. On the seventh day seedlings were placed in the light at 28±2° C.

Cocultivation and Plant Regeneration

Single colonies of *A. tumefaciens* strain 2760 containing binary plasmids pCGN2917 and pCGN2926 were transferred to 5 ml of MG/L broth and grown overnight at 30° C. Bacteria cultures were diluted to 1×10$^8$ cells/ml with MG/L just prior to cocultivation. Hypocotyls were excised from eight day old seedlings, cut into 0.5–0.7 cm sections and placed onto tobacco feeder plates (Horsch et al. 1985). Feeder plates were prepared one day before use by plating 1.0 ml tobacco suspension culture onto a petri plate containing Callus Initiation Medium CIM without antibiotics (MS salts: B5 vitamins: 3% glucose: 0.1 mg/L 2,4-D: 0.1 mg/L kinetin: 0.3% gelrite, pH adjusted to 5.8 prior to autoclaving). A sterile filter paper disc (Whatman #1) was placed on top of the feeder cells prior to use. After all sections were prepared, each section was dipped into an A. tumefaciens culture, blotted on sterile paper towels and returned to the tobacco feeder plates.

Following two days of cocultivation on the feeder plates, hypocotyl sections were placed on fresh Callus Initiation Medium containing 75 mg/L kanamycin and 500 mg/L carbenicillin. Tissue was incubated at 28±2° C., 30 uE 16:8 light:dark period for 4 weeks. At four weeks the entire explant was transferred to fresh callus initiation medium containing antibiotics. After two weeks on the second pass, the callus was removed from the explants and split between Callus Initiation Medium and Regeneration Medium (MS salts: 40 mM KNO$_3$: 10 mM NH$_4$Cl: B5 vitamins: 3% glucose: 0.3% gelrite: 400 mg/L carb: 75 mg/L kanamycin).

Embryogenic callus was identified 2–6 months following initiation and was subcultured onto fresh regeneration medium. Embryos were selected for germination, placed in static liquid Embryo Pulsing Medium (Stewart and Hsu, medium: 0.01 mg/1 NAA: 0.01 mg/L kinetin: 0.2 mg/L GA3) and incubated overnight at 30° C. The embryos were blotted on paper towels and placed into Magenta boxes containing 40 mls of Stewart and Hsu medium solidified with Gelrite. Germinating embryos were maintained at 28±2° C. 50 uE m$^{-2}$s$^{-1}$ 16:8 photoperiod. Rooted plantlets were transferred to soil and established in the greenhouse.

Cotton growth conditions in growth chambers are as follows: 16 hour photoperiod, temperature of approximately 80–85°, light intensity of approximately 500 µEinsteins. Cotton growth conditions in greenhouses are as follows: 14–16 hour photoperiod with light intensity of at least 400 µEinsteins, day temperature 90–95° F., night temperature 70–75° F., relative humidity to approximately 80%.

Plant Analysis

Flowers from greenhouse grown Tl plants were tagged at anthesis in the greenhouse. Squares (cotton flower buds), flowers, bolls etc. were harvested from these plants at various stages of development and assayed for GUS activity. GUS fluorometric and histochemical assays were performed on hand cut sections as described in Jefferson (1987), supra.

At least ten events (transgenic plants) from each construct (pCGN2917 and pCGN2926) were sent to the Growth Chambers/Greenhouse. Approximately 80% (9/11) of the 2917 plants and 100% (12/12) of the 2926 plants expressed GUS at a level detectable by either fluorometric or histochemical assay. Squares from several of pCGN2917 and pCGN2926 transfected plants were assayed for GUS expression using histochemical analysis wherein the cells which are expressing GUS stain blue. Preliminary analysis indicates that all plants expressed GUS in the developing floral parts. Ovules and anthers stained extremely dark. Bracts and locule walls were also blue in some cases. Fibers from 5, 9 and 12 DPA bolls off these plants were also expressing GUS.

Several GUS assays were done on developing bolls at stages from squaring through 53 days post anthesis. GUS activity is very high in squares and flowers. Activity in bolls varies from plant to plant. Activity was present in fiber from two of the 2926 plants at 43 and 53 dpa.

β-glucuronidase is a very stable enzyme; therefore, presence of GUS activity may not be directly correlated in a temporal manner with gene expression, however, the specificity of expression in tissues and/or structures derived from ovary integument was significant. Other tissues not derived from ovary integument, showed no GUS activity above background. Differences in the breakdown of GUS as well as differences in expression may explain the variability of expression patterns.

Comparisons between Cotton and Tomato Expression

An initial MUG assay was done on tissues from tomato and cotton plants transfected with pCGN2917 and pCGN2918. GUS activity was found in tomato roots, stems and leaves as well as meristems, and floral parts. The amount of activity varied from plant to plant. In cotton, activity was highest in floral parts but was detectable in roots and stems of some plants.

T2 tomato plants from 2926 and 2917 are being tagged at anthesis. These plants have been tested for both kan and GUS expression. As the tissue matures it will be assayed and photographed.

EXAMPLE 10

Expression of Transaenic Melanin Synthesis Genes

A binary construct for plant transformation to express genes for melanin synthesis is prepared as follows. The mel operon of Streptomyces antibioticus (Bernan et al. (1985) 34:101–110) is subcloned as a BclI fragment into a Bluescript vector. NcoI and BanHI sites are inserted by mutagenesis immediately 5' to (and including) the ATG initiation codon for ORF438. The resulting plasmid is pCGN4229. pCGN4229 is further mutagenized by inserting a PstI site immediately following the ORF438 stop codon and by the addition of NcoI and BamHI sites at the start codon of the tyrA locus, thus, providing the mutagenized mel operon. A PstI site from the plasmid vector is similarly located immediately 3' to the tyrA encoding region.

The pZ130 cassette, pCGN2909, is mutagenized to reinsert the NcoI site including the ATG codon for the initial MET of the pZ130 encoded sequence, and results in pCGN4228. pCGN4228 is mutagenized to delete the BamHI site at the 3' end of the pZ130 transcriptional termination region and to insert an AscI linker fragment in its place, resulting in pCGN4235. pCGN4228 is also mutagenized to deleted the 3' BamHI site and insert an AscI linker 5' to the pZ130 transcriptional initiation region (at XhoI/SalI digested and Klenow treated pCGN4228) resulting in pCGN4241.

The Streptomyces ORF438 region is obtained by digestion of the mutagenized mel operon construct with NcoI and PstI and inserted into Nco/Pst digested pCGN4235. The tyrA region is cloned as an NcoI/PstI fragment from the mutagenized mel operon construct into Nco/Pst digested pCGN4241.

A fragment of the tobacco ribulose bisphosphate carboxylase small subunit gene encoding the transit peptide and 12 amino acids of the mature protein is inserted in reading frame with the ORF438 encoding sequence as an NcoI/BamHI fragment. The fragment is similarly inserted in front of the tyrA encoding sequence. The resulting constructs contain the transit peptide/ORF438 and transit peptide/tyrA fusions positioned for expression from the pZ130 5' and 3' regulatory regions.

A binary vector (See FIG. 7) for insertion of the ORF438 and tyrA constructs is prepared from pCGN1578 (McBride et al., supra) by substitution of the pCGN1578 linker region with a linker region containing the following restriction digestion sites:Asp718/Asc/Pac/XbaI/BamHI/Swa/Sse/HindIII. (See FIG. 8). This results in pCGN1578PASS. Asc, Pac, Swa and Sse are restrictive enzymes that cut at the 8-base recognition sites. The enzymes are available from New England BioLabs: Asc, Pac; Boehringer Manheim:Swa; and Takara (Japan):Sse.

The ORF438 pZ130 construct is inserted into pCGN1578PASS as an Asp/Asc fragment. The tyrA pZ130 construct is inserted adjacent to the ORF438 pZ130 construct as an Asc/Xba fragment.

EXAMPLE 11

Expression of Transaenic Melanin Synthesis Genes in Tobacco Plants

Transgenic tobacco plants were generated using techniques and DNA constructs as provided in Examples 8–10.

A set of untransformed plants was utilized as a control. All of the untransformed control plants utilized in this following experiment exhibited normal growth and development phenotypes. (See Table 1.)

A first set of transgenic plants was obtained using binary vector pCGN4269 which expressed both the ORF438 and tyrA genes involved in melanin synthesis in the cytosol of these tobacco plants. Transgenic plants obtained using pCGN4269 contained a DNA construct containing the pZ130 transcriptional and translational region from tomato which was used to drive expression of the OFR438 and tyrA gene products. Cytosol-specific expression of the melanin synthesis genes yielded transgenic plants having a normal phenotype as compared to untransformed control tobacco. (Table 1.) Melanin synthesis is not detectable in these plants as the substrates for melanin production are not expected to be present at high levels in the cytosol.

A second set of transgenic plants was obtained using binary vector pCGN4272 which specifically targeted the polypeptides expressed from the melanin synthesis genes to the plastids of these plants. Transgenic plants transformed with pCGN4272 contained a DNA construct containing the tomato pZ130 transcriptional and translational initiation region and DNA encoding a tobacco SSU transit peptide and a 6 amino acid region of the mature SSU polypeptide coupled to the OFR438 gene and DNA encoding a tobacco SSU transit peptide and a 6 amino acid region of the mature SSU polypeptide coupled to the tyrA gene. The transit peptide was used to direct the transport of the ORF438 and tyrA gene products to the plastids of these plants. Plastid-targeted expression of the melanin synthesis ORF438 and tyrA products resulted in plants having altered phenotype (see Table 1). The phenotypic alterations included meristem abortion, stunted growth, narrow leaves, and new leaf curling. Alteration of plant color was also observed: some of the transgenic plants exhibited meristem yellowing and black streaks over various portions of the plant and different meristimatic regions relative to control plants. In addition, the basal flower buds of these transgenic plants were extremely dark compared to those transgenic plants which expressed the cytosol-specific melanin synthesis gene products or compared to control plants. The pZ7 promoter is known to result in foreign gene expression in ovary and meristem derived tissue. The observation of this phenotype is believed to be due to depletion of the tyrosine amino acid pools in the plastid and/or the effect of auxin-like melanin compounds on plant growth and development.

TABLE 1

| Number of Plants Generated Phenotype | Plants Having Altered |
|---|---|
| Control | 20 | 0 |
| Cytosol-Specific DNA Construct | 40 | 0 |
| Plastid-Specific DNA Construct | 52 | 40 |

EXAMPLE 12

Constructs for Targeting Pigment Synthesis Genes

Constructs which contain encoding sequences for bacterial genes involved in biosynthesis of pigmented compounds and sequences for directing transport of the encoded proteins into plastids or vacuoles are prepared. The sequences are manipulated to be present on an NcoI/EcoRI fragment which may then be further manipulated to add transcriptional initiation regions useful for providing transcription in plant tissues. Examples of useful promoters include pZ7, T7 (for plastid expression), and various promoters capable of providing for expression in cotton fibers or plant flower petals.

For plastid targeting, the constructs contain a fragment of the tobacco ribulose bisphosphate carboxylase small subunit gene encoding the transit peptide and 12 amino acids of the mature protein (Tssu) positioned in reading frame with the appropriate encoding sequence. For production of indigo, pCGN5128 (Tssu::tna) and pCGN5129 (Tssu::pig) find use for plastid targeting. The designation tna stands for the gene encoding tryptophanase from *E. coli,* an enzyme which converts tryptophan to indole (Stewart et al., (1986) *J Bacteriol* 166:217–223). The pig designation is used for the encoding sequence to the protein for indigo production from Rhodococcus, which produces indigo from indole (Hart et a (1990) *J Gen Microbiol* 136:1357–1363). Both tna and pig obtained by PCR. In pCGN5128 and pCGN5129 the transit SSU includes the tobacco 54 amino acid transit peptide plus 12 amino acids from the mature small subunit protein.

For production of melanin in plants, constructs pCGN5075 (Tssu::TyrA) and pCGN5076 (Tssu::ORF438) find use for plastid targeting. In this approach melanin synthesis comes from the expression of two proteins from *Streptomyces antibioticus,* the tyrA which converts tyrosine to melanin and the ORF438, which is believed to assist the tyrA enzyme in copper binding (Bernan et al., (1985) Gene 37:101–110). Both proteins were obtained by PCR. In pCGN5076 and pCGN5075 the transit from SSU also includes the tobacco 54 amino acid transit peptide plus 12 amino acids from the mature small subunit.

For vacuolar targeting of the melanin synthesis genes, constructs include a fragment of the metallocarboxypeptidase inhibitor gene, encoding the entire 32 amino acid N-terminus signal peptide of that protein plus 6 amino acids of the mature protein (CPI+6) (Martineau et al., supra), positioned in reading frame with the appropriate encoding sequences. In addition to the signal peptide, a sequence encoding a vacuolar localization signal (VLS) is inserted 3' of the protein encoding sequence. Thus, for melanin production in vacuoles, CPI+6::tyrA::VLS and CPI+6::ORF438::VLS are used. In this example, the VLS utilized is the 8 amino acids obtained from beyond the C terminus of the metallocarboxypeptidase inhibitor gene described in Martineau et al.

As shown by the above results, expression of a gene of interest can be obtained in cells derived from ovary cells, including tomato fruit and cotton fibers, and expression of genes involved in synthesis of pigments combined with appropriate targeting sequences results in modification of color phenotype in the selected plant tissue.

All publications and patent applications cited in this specification are herein incorporated by reference as if each individual publication or patent application were specifically and individually indicated to be incorporated by reference.

Although the foregoing invention has been described in some detail, by way of illustration and example for purposes of clarity and understanding, it will be readily apparent to those of ordinary skill in the art that certain changes and modifications may be made thereto, without departing from the spirit or scope of the appended claims.

What is claimed is:

1. A DNA construct comprising as operably joined components in the direction of transcription, a tomato pZ7 promoter, a transport signal encoding sequence from a plant nuclear-encoded gene, and an open reading frame encoding an enzyme required for synthesis of a pigment.

2. A plant cell comprising the DNA construct of claim 1.

3. A plant comprising the cell of claim 2.

4. The DNA construct according to claim 1 wherein said transport signal encoding sequence encodes a plastid transit peptide.

5. The DNA construct according to claim 4, wherein said transport signal encoding sequence further comprises a portion of the mature protein encoding region for said plant nuclear-encoded gene.

6. The DNA construct according to claim 1 wherein said transport signal encoding sequence encodes a signal peptide which provides for transport across the rough endoplasmic reticulum.

7. The DNA construct according to claim 6, wherein said DNA sequence further comprises, 3' to said open reading frame, a vacuolar localization signal.

8. The DNA construct of claim 1 wherein said pigment is melanin or indigo.

9. The DNA construct of claim 8 wherein said open reading frame is from a bacterial gene.

10. The DNA construct of claim 9 wherein said bacterial gene is selected from the group consisting of ORF438, tyrA, pig, and tna.

11. A plant cell comprising the DNA construct according to anyone of claims 4–10.

12. A plant comprising a cell of claim 11.

13. A method of modifying color phenotype in a cotton fiber tissue, said method comprising:
    transforming a plant cell with DNA comprising a construct for expression of a protein in a melanin biosynthesis pathway, wherein said construct comprises as operably joined components:
    i) a promoter for transcription in a cotton fiber cell,
    ii) a transport signal encoding a plastid transit peptide,
    iii) a tyrA or an ORF438 open reading frame, and
    iv) a transcriptional termination region functional in cells of said cotton fiber tissue, wherein said cotton fiber tissue comprises a substrate of a protein encoded by tyrA or ORF438; and
    growing said plant cell to produce a plant comprising said cotton fiber tissue, wherein said protein reacts with said substrate to produce melanin.

14. A method of modifying color phenotype in a cotton fiber tissue, said method comprising:
    transforming a plant cell with DNA comprising constructs for expression of two proteins in a melanin biosynthesis pathway, wherein each construct comprises as operably joined components:
    i) a promoter for transcription in a cotton fiber cell,
    ii) a transport signal encoding a signal peptide which provides for transport across the rough endoplasmic reticulum,
    iii) tyrA and ORF438 open reading frames, and
    iv) a transcriptional termination region functional in cells of said cotton fiber tissue, wherein said cotton fiber tissue comprises substrate of proteins encoded by tyrA and ORF438; and
    growing said plant cell to produce a plant comprising said cotton fiber tissue, wherein said proteins react with said substrate to produce melanin.

15. A method of modifying color phenotype in a cotton fiber tissue, said method comprising:
    transforming a plant cell with DNA comprising a construct for expression of a protein in a pigment biosynthesis pathway, wherein said construct comprises as operably joined components:
    i) a tomato pZ7 promoter,
    ii) a transport signal encoding sequence from a plant nuclear-encoded gene,
    iii) an open reading frame encoding a protein required for synthesis of a pigment, and
    iv) a transcriptional termination region functional in cells of said cotton fiber tissue, wherein said cotton fiber tissue comprises a substrate of said protein; and
    growing said plant cell to produce a plant comprising said cotton fiber tissue, wherein said protein reacts with said substrate to produce said pigment.

16. The method of claim 15 wherein said transport signal encoding sequence encodes a plastid transit peptide.

17. The method of claim 16 wherein said DNA comprises constructs for expression of two proteins in a pigment biosynthesis pathway, wherein each of said constructs comprises components i) through iv), and wherein said two proteins are not encoded by the same gene.

18. The method of claim 15 wherein said transport signal encoding sequence encodes a signal peptide which provides for transport across the rough endoplasmic reticulum.

19. The method of claim 18 wherein said DNA comprises constructs for expression of two proteins in a pigment biosynthesis pathway, wherein each of said constructs comprises components i) through iv), and wherein said two proteins are not encoded by the same gene.

20. The method of claim 17 or 19 wherein said pigment is melanin and said proteins are encoded by tyrA and ORF438.

21. A method of modifying color phenotype in a cotton fiber tissue, said method comprising:

transforming a plant cell with DNA comprising constructs for expression of two proteins in a melanin biosynthesis pathway, wherein each construct comprises as operably joined components:
  i) an ovary tissue promoter that directs transcription prior to anthesis through flower senescence in a cell that will develop into a cotton fiber cell,
  ii) a transport signal encoding a signal peptide which provides for transport across the rough endoplasmic reticulum,
  iii) tyrA and ORF438 open reading frames, and
  iv) a transcriptional termination region functional in cells of said cotton fiber tissue, wherein said cotton fiber tissue comprises substrate of proteins encoded by tyrA and ORF438; and growing said plant cell to produce a plant comprising said cotton fiber tissue, wherein said proteins react with said substrate to produce melanin.

22. A method of modifying color phenotype in a cotton fiber tissue, said method comprising:

transforming a plant cell with DNA comprising a construct for expression of a protein in a melanin biosynthesis pathway, wherein said construct comprises as operably joined components:
  i) an ovary tissue promoter that directs transcription in a cell that will develop into a cotton fiber cell prior to anthesis through flower senescence,
  ii) a transport signal encoding a plastid transit peptide,
  iii) a tyrA or an ORF438 open reading fame, and
  iv) a transcriptional termination region functional in cells of said cotton fiber tissue, wherein said cotton fiber tissue comprises a substrate of a protein encoded by tyrA or ORF438; and growing said plant cell to produce a plant comprising said cotton fiber tissue, wherein said protein reacts with said substrate to produce melanin.

* * * * *

SEQUENCE LISTING (1) GENERAL INFORMATION:

(iii) NUMBER OF SEQUENCES:  6

(2) INFORMATION FOR SEQ ID NO:1:

(i) SEQUENCE CHARACTERISTICS:
      (A) LENGTH: 564 base pairs
      (B) TYPE:   nucleic acid
      (C) STRANDEDNESS:  double
      (D) TOPOLOGY:     linear (ii) MOLECULE TYPE:  cDNA to mRNA (xi) SEQUENCE DESCRIPTION: SEQ ID NO:  1:

```
AAA AAA ACA AAA ACA TTT CTA ATC TTT TTC ACT CAT TCC ATG GCT CGT       48
Lys Lys Thr Lys Thr Phe Leu Ile Phe Phe Thr His Ser Met Ala Arg
 1               5                  10                  15

TCC ATT TTC TTC ATG GCA TTT TTG GTC TTG GCA ATG ATG CTC TTT GTT       96
```

```
Ser Ile Phe Phe Met Ala Phe Leu Val Leu Ala Met Met Leu Phe Val
         20                  25                  30

ACC TAT GAG GTA GAA GCT CAG CAA ATT TGC AAA GCA CCA AGC CAA ACT    144
Thr Tyr Glu Val Glu Ala Gln Gln Ile Cys Lys Ala Pro Ser Gln Thr
         35                  40                  45

TTC CCA GGA TTA TGT TTT ATG GAC TCA TCA TGT AGA AAA TAT TGT ATC    192
Phe Pro Gly Leu Cys Phe Met Asp Ser Ser Cys Arg Lys Tyr Cys Ile
 50                  55                  60

AAA GAG AAA TTT ACT GGT GGA CAT TGT AGC AAA CTC CAA AGG AAG TGT    240
Lys Glu Lys Phe Thr Gly Gly His Cys Ser Lys Leu Gln Arg Lys Cys
 65                  70                  75                  80

CTA TGC ACT AAG CCA TGT GTA TTT GAC AAA ATC TCA AGT GAA GTT AAA    288
Leu Cys Thr Lys Pro Cys Val Phe Asp Lys Ile Ser Ser Glu Val Lys
                 85                  90                  95

GCA ACT TTG GGT GAG GAA GCA AAA ACT CTA AGT GAA GTT GTG CTT GAA    336
Ala Thr Leu Gly Glu Glu Ala Lys Thr Leu Ser Glu Val Val Leu Glu
            100                 105                 110

GAA GAG ATT ATG ATG GAG TAATAA TTA AGT GAG GTT AAA TAA GGA TTT    384
Glu Glu Ile Met Met Glu        Leu Ser Glu Val Lys     Gly Phe
            115                     120                     125

TGA GTG TCA AAA AAA ACA AAA TTA ATA AAG TGT TGC CTT TTC TTA TTA    432
Val Ser Lys Lys Thr Lys Leu Ile Lys Cys Cys Leu Phe Leu Leu
                130                 135                 140

GGG TAG CTT GTG ATG TTG TGT TAG TAT TGG CCT ATA GTA GCC ATT TGA    480
Gly     Leu Val Met Leu Cys     Tyr Trp Pro Ile Val Ala Ile
                    145                     150

CAC ATT AAA TAA GTT TGT GAC ACA TCA TTA ATC CTT ATG TAT GTA TGT    528
His Ile Lys     Val Cys Asp Thr Ser Leu Ile Leu Met Tyr Val Cys
155                     160                 165

TTT AAT GAA AAA TGA TCG ACT ACG ATC TTT AAT TTT                    564
Phe Asn Glu Lys     Ser Thr Thr Ile Phe Asn Phe
170                     175
```

(2) INFORMATION FOR SEQ ID NO:2:

(i) SEQUENCE CHARACTERISTICS:
        (A) LENGTH: 3528 base pairs
        (B) TYPE:   nucleic acid
        (C) STRANDEDNESS: double
        (D) TOPOLOGY:     linear (ii) MOLECULE TYPE:   genomic DNA (xi) SEQUENCE DESCRIPTION: SEQ ID NO:2:

```
GCTCCACTAC TCTCATCACT TTAGTTCATC AAGCCTTCTT TTATACCAAG GCATCATCAA     60

TCTCATTAAC AAAGTAGATT AGGGTTTTTC AAGATTTAGG ATTCAATAGC TTCATCATGC    120

TTATTTTATC ACAATTATAT AATCACATTC ATACAAGCAT ACAATTAAGC ATATAGAAGG    180

GTTTACAATA CTACCCAATA CATATCATTC GCTATTAAGA GTTTACTACG AATAGCATAA    240

ACCATAACCT ACCTCCACCG AAGAATCGCG ATCAAACAAT CTACTTTCCC AAAGCTGCGT    300

TCTTCTTCGT TTTCTCTCTC TCTTGATCGT TCGTTTCTCC CTCTCTTTGT TCTTTCTATT    360

TTTCTTATTC AAACCCTCTT TCTTTTACCC TAATTAGTAT ATAATTAAGT ATAAAAGATG    420

ATAAAATACC CCATCTATTT GTTTGAAGGT TATCTCTTTT AGCCCCCAAG TAATTGAATT    480

ATTAACATTA AACCACTAAC TTTATAATTA TAAGCAGGAA TAGTCCAAAA CGCCCCTTAA    540

AATATTTAAC AGAAATCCGA CCCAGTCAGG GTCACGCAGC CTGTANCGGN NCACAACTGT    600

GACGGTCCGT CCTGCATGGC CGTCACAAAG TTCAGAGAGT TAATTTCTGT GGAAGATGTG    660

TANGGTNGTC GTGCCCACGA CGGTCCGTCC TGTCATTTCG TTACGAAGTT CAGAGAGTCG    720
```

```
ATTTCAGTAC CCAAATTTCA GAATTCTAAG TGTTTTGGAA CGAGACCCCN CGGTCCGTCG    780
TGCCCATGAC GGTTCGTCGT GGGATCCGTC GACTCAGCCA GTTTTTCCAA AATTAAAATC    840
TGCTGCTCAA AACGACTAAA CAGGTCGTTA CAAAGTACTC AATCAAATAA AAAGAATAAA    900
TTCTTTTCCA AATACATATA TTGTTTATAG GACAGTGTTA ACAGGGAAAT GTAATCGTTG    960
CCTCAATCGA TTTTTTTTTT TGAAATTAAG ATTGATTAGA TCTTCTTTAA GATAACAATG   1020
TCTCAAAGAT AAATTGAATG AATGAATTAG CTATATTATC ATTTGAAAAG AAATTACTAA   1080
AACAGATTGA TAATAAAATA ATAATAAATG ACTTTGCATC TAAAATAGCT AGAAAGCAGA   1140
TTTTTAAATA AAAATACATA TGATAAAAAA AAGATAAATT AGAGTCATCC CATAAATTTC   1200
GCTTTAGGCC CCCAATGTTG TTAAGTCGGC CCTGAAAATA GGAATGGTAT TAAATATTTT   1260
GTTTTGATTT CACACTTGAT ATTTGACATT CATATTAGAA AATAATTAAA TTTATATTCG   1320
TGTAGAGTGG TCTCACATTA ATGGGTAAAA TATTTCCACA CAAAAACTAT TTTACAATCA   1380
TAGCTAGAAT CTGAAATATC TAATGTACTC CACCCAATTA ATTAAAGATG ATTTTTTTGC   1440
TTAAATAATA AAAATATGTC TATTGCCAAA CTACTAATAG ATGTACTCAC AAAAAAAATA   1500
AAATAAAAAA TCAAGTGTAT ATACAATGAT TCGGAAGGCC ATTTTTGAAA ATTTTCATAA   1560
AATGACCGTT TTACCCGTTC ACAATTGTTG TTTCAGCATT TTTGTTTGGT TTGTGGATTT   1620
GGTTATGGAA GTTCAATAAA AAGTTGTGGT TTTATAAGCT TTGGAGTTTT GAAAGGTTTA   1680
AGTTGATTAA AAGTAGTTTT TAGTGTCAAT TGGAGTTTCG TGTCTTGAAA TAAATTTTAT   1740
CACTTGCATT AGTTTCAAAA TGTCGAGTTT GGTTAAGTAG AGGTTTTTTT CATTCGGAGT   1800
TTTTTTATGA ATTTAAAATG TTAAGCTGAA AGTTTATGAA ATTTTAGCCT TTGAGTTAAT   1860
TTTGATGCTT GAATTAAATT TTTGAGAATT TTTTTGAAAT CTGGGGATAA TGTTAGGTCT   1920
TAGAGAAGTC TGGTTGAATT TTCATAGCTC AAGAGATTAG TTTTGACTTT TTAGGCATTT   1980
TGTTGGTTTA TTACGATTTT CACGGACTTT CGAATTAAGG AGACTTCAAA ATTCATATTT   2040
AATGGTTCGT GTGTTCGTTA GTTTTAAAAA TCGTGTCTTT ATAAGGATTT ATACTTAAAA   2100
AAATAAAATA AAATAAAGTA CTACTAACAT GTAATTCTGT CATAAGATAA GGTTGTACAT   2160
TTAGGACTAT TTGAATATTC ATCAAAAATA AAAAAAAGTA GAGATGATAG TAATATAAAT   2220
ATTTATTTTT GATTTTACAT TTGATATTTT AATACTAACA ATATGACATA ATAAAATTTG   2280
TATTCAGATT GTAAAATATT CCCTAAAAAA AGATACTTTT ACTGTGGTGG CTCAAATTCA   2340
AAATTTTCTA AGAAAAACTA CTAATAATTG ATTTCTAATT AAAATTTCGA TATATATATA   2400
TATATATATA TATATATCAT AATATACTTC ACCTACCTCA ATTATTATTA TTTTCTTTTT   2460
TTTTTACTTC ACATATTTTT GGSCSACCAA TTTTTTTTTT AACTTTTTTG GTCTTACTCT   2520
TATTTCACTC CCTATAAATA ACTCCCATTG TGTGATATTT TTATTCACAA CTCTAACTTA   2580
CAATCTTTCT TATTATTAAA AAAAACAAAA ACATTTCTAA TCTTTTTCAC TCATTCCATG   2640
GCTCGTTCCA TTTTCTTCAT GGCATTTTTG GTCTTGGCAA TGATGCTCTT TGTTACCTAT   2700
GGTTTGTCTT CATAATTTAT TCCTCTAAAA TCATCGCAAT AAAAAAAAAA TGTAACGAAG   2760
CAGACATCAG TAAACCGTTT AAATAAACCC TAAAAAAATT GTGAATTGAT ATTACTTGCT   2820
ATACGTTTAA CAACTATGAT AAAAAAACCC TAAAATATAC TTATTTCGAT TTCGTCTCTC   2880
TCATGTTATT CTAACTATTT TTTGTGTGTG AATGATTGTA GAGGTAGAAG CTCAGCAAAT   2940
TTGCAAAGCA CCAAGCCAAA CTTTCCCAGG ATTATGTTTT ATGGACTCAT CATGTAGAAA   3000
ATATTGTATC AAAGAGAAAT TTACTGGTGG ACATTGTAGC AAACTCCAAA GGAAGTGTCT   3060
```

```
ATGCACTAAG CCATGTGTAT TTGACAAAAT CTCAAGTGAA GTTAAAGCAA CTTTGGGTGA    3120

GGAAGCAAAA ACTCTAAGTG AAGTTGTGCT TGAAGAAGAG ATTATGATGG AGTAATAATT    3180

AAGTGAGGTT AAATAAGGAT TTTGAGTGTC AAAAAAAACA AAATTAATAA AGTGTTGCCT    3240

TTTCTTATTA GGGTAGCTTG TGATGTTGTG TTAGTATTGG CCTATAGTAG CCATTTGACA    3300

CATTAAATAA GTTTGTGACA CATCATTAAT CCTTATGTAT GTATGTTTTA ATGAAAAATG    3360

ATCGACTACG ATCTTTAATT TTATGTTTTA CATTTAATTA ATCACTTTCT GTTACGATTC    3420

ATTTATCTAG TTATGAATGA AATATAGAGT GATTTGAAGT AAGGAGCTAG TCTTCAAACA    3480

AAGACGTACA TATGTACAAA GTAGGGTACT ATTAAACTTC TTTTTTAT               3528
```

(2) INFORMATION FOR SEQ ID NO:3:

(i) SEQUENCE CHARACTERISTICS:
        (A) LENGTH:    453 base pairs
        (B) TYPE:      nucleic acid
        (C) STRANDEDNESS:  double
        (D) TOPOLOGY:    linear (ii) MOLECULE TYPE:   cDNA to mRNA (xi) SEQUENCE DESCRIPTION: SEQ ID NO: 3:

```
ATTATTATTA CC ATG GCA CAA AAA TTT ACT ATC CTT TTC ACC ATT CTC CTT      51
              Met Ala Gln Lys Phe Thr Ile Leu Phe Thr Ile Leu Leu
               1               5                  10

GTG GTT ATT GCT GCT CAA GAT GTG ATG GCA CAA GAT GCA ACT CTG ACG        99
Val Val Ile Ala Ala Gln Asp Val Met Ala Gln Asp Ala Thr Leu Thr
 15                  20                  25

AAA CTT TTT CAG CAA TAT GAT CCA GTT TGT CAC AAA CCT TGC TCA ACA       147
Lys Leu Phe Gln Gln Tyr Asp Pro Val Cys His Lys Pro Cys Ser Thr
 30                  35                  40                  45

CAA GAC GAT TGT TCT GGT GGT ACG TTC TGT CAG GCC TGT TGG AGG TTC       195
Gln Asp Asp Cys Ser Gly Gly Thr Phe Cys Gln Ala Cys Trp Arg Phe
                     50                  55                  60

GCG GGG ACA TGT GGG CCC TAT GTT GGG CGC GCC ATG GCC ATA GGC GTG       243
Ala Gly Thr Cys Gly Pro Tyr Val Gly Arg Ala Met Ala Ile Gly Val
                 65                  70                  75

TGATTACAAT TTCGTTGTTC TTCTTTTTCG ACTTTTTAAT CCCAAGTGAA TAAAGTCTAA     303

TTCGAAAAAG AAGAAAAAAG TATCTATGTC TGAGTTATAT GTTTTGTGGC TAATAAGAAA     363

TCGACTATGC TTGTTGATTT GATAAAAATT ATGTCATTAG GGTGTGATAT GTAATCATCA     423

AATTAAATAA AAATCATCGC ATTGTGTGTG                                     453
```

(2) INFORMATION FOR SEQ ID NO:4:

(i) SEQUENCE CHARACTERISTICS:
        (A) LENGTH:    36 base pairs
        (B) TYPE:      nucleic acid
        (C) STRANDEDNESS:  single
        (D) TOPOLOGY:    linear (ii) MOLECULE TYPE:   other nucleic acid
        (A) DESCRIPTION:  synthetic oligonucleotide (xi) SEQUENCE DESCRIPTION: SEQ ID NO: 4:

```
AATTAGATGC AGGTCCATAA GTTTTTTCTA GACGCG                               36
```

(2) INFORMATION FOR SEQ ID NO:5:

(i) SEQUENCE CHARACTERISTICS:
        (A) LENGTH:    42 base pairs
        (B) TYPE:      nucleic acid

```
            (C) STRANDEDNESS:  single
            (D) TOPOLOGY:      linear (ii) MOLECULE TYPE:     other nucleic acid
            (A) DESCRIPTION:  synthetic oligonucleotide (xi) SEQUENCE DESCRIPTION: SEQ ID NO: 5:

GTTCCTGCAG CATGCCCGGG ATCGATAATA ATTAAGTGAG GC                       42

(2) INFORMATION FOR SEQ ID NO:6:

(i) SEQUENCE CHARACTERISTICS:
            (A) LENGTH:    25 base pairs
            (B) TYPE:      nucleic acid
            (C) STRANDEDNESS:  single
            (D) TOPOLOGY:      linear (ii) MOLECULE TYPE:     other nucleic acid
            (A) DESCRIPTION:  synthetic oligonucleotide (xi) SEQUENCE DESCRIPTION: SEQ ID NO: 6:

CAAGAATTCA TAATATTATA TATAC                                          25
```